(12) United States Patent
Chiosis et al.

(10) Patent No.: US 10,336,757 B2
(45) Date of Patent: Jul. 2, 2019

(54) TREATMENT OF NEURODEGENERATIVE DISEASES THROUGH INHIBITION OF HSP90

(75) Inventors: Gabriela Chiosis, New York, NY (US); Paul Greengard, New York, NY (US); Fei Dou, Nanjing (CN); Wenjie Luo, Hopatcong, NJ (US); Huazhong He, New York, NY (US); Danuta Zatorska, Ericeira (PT)

(73) Assignees: Sloan-Kettering Institute for Cancer Research, New York, NY (US); The Rockefeller University, New York, NY (US)

( * ) Notice: Subject to any disclaimer, the term of this patent is extended or adjusted under 35 U.S.C. 154(b) by 1326 days.

(21) Appl. No.: 12/307,063

(22) PCT Filed: Jul. 2, 2007

(86) PCT No.: PCT/US2007/072671
§ 371 (c)(1),
(2), (4) Date: Dec. 30, 2008

(87) PCT Pub. No.: WO2008/005937
PCT Pub. Date: Jan. 10, 2008

(65) Prior Publication Data
US 2009/0298857 A1 Dec. 3, 2009

Related U.S. Application Data

(60) Provisional application No. 60/806,427, filed on Jun. 30, 2006.

(51) Int. Cl.
*A01N 43/90* (2006.01)
*A61K 31/52* (2006.01)
*A01N 43/54* (2006.01)
*C07D 239/42* (2006.01)
*C07D 401/04* (2006.01)
*A01N 43/50* (2006.01)
*A61K 31/415* (2006.01)
*A01N 43/30* (2006.01)
*A61K 31/36* (2006.01)
*C07D 473/40* (2006.01)

(52) U.S. Cl.
CPC ............ *C07D 473/40* (2013.01); *A61K 31/52* (2013.01)

(58) Field of Classification Search
USPC ....................................................... 514/263
See application file for complete search history.

(56) References Cited

U.S. PATENT DOCUMENTS

| 7,241,890 | B2 | 7/2007 | Kasibhatla et al. |
| 7,834,181 | B2 | 11/2010 | Chiosis et al. |
| 8,703,942 | B2 | 4/2014 | Chiosis et al. |
| 9,328,114 | B2 | 5/2016 | Chiosis et al. |
| 9,346,808 | B2 | 5/2016 | Sun et al. |
| 9,403,828 | B2 | 8/2016 | Chiosis |
| 9,546,170 | B2 | 1/2017 | Taldone et al. |
| 9,701,678 | B2 | 7/2017 | Chiosis et al. |
| 9,926,321 | B2 | 3/2018 | Sun et al. |
| 10,000,494 | B2 | 6/2018 | Chiosis et al. |
| 2005/0004026 | A1 | 1/2005 | Kasibhatla et al. |
| 2005/0049263 | A1 | 3/2005 | Kasibhatla et al. |
| 2005/0107343 | A1 | 5/2005 | Kasibhatla et al. |
| 2005/0113339 | A1 | 5/2005 | Kasibhatla et al. |
| 2005/0113340 | A1 | 5/2005 | Kasibhatla et al. |
| 2005/0119292 | A1 | 6/2005 | Gravestock et al. |
| 2005/0256183 | A1 | 11/2005 | Kasibhatla et al. |
| 2006/0211737 | A1 | 9/2006 | Huang et al. |
| 2007/0299258 | A1 | 12/2007 | Bajji et al. |
| 2008/0096903 | A1 | 4/2008 | Chen et al. |
| 2008/0221132 | A1 | 9/2008 | Cai et al. |
| 2008/0234297 | A1 | 9/2008 | Qian et al. |
| 2008/0234314 | A1 | 9/2008 | Cai et al. |
| 2008/0253965 | A1* | 10/2008 | Chiosis et al. ............... 424/1.85 |
| 2009/0298857 | A1 | 12/2009 | Chiosis et al. |
| 2011/0104054 | A1 | 5/2011 | Chiosis et al. |
| 2011/0312980 | A1 | 12/2011 | Chiosis |
| 2012/0208806 | A1 | 8/2012 | Chiosis et al. |
| 2014/0045867 | A1 | 2/2014 | Taldone et al. |
| 2014/0088121 | A1 | 3/2014 | Sun et al. |
| 2014/0227183 | A1 | 8/2014 | Chiosis et al. |
| 2014/0343037 | A1 | 11/2014 | Huang et al. |
| 2014/0378452 | A1 | 12/2014 | Chiosis |
| 2016/0194328 | A1 | 7/2016 | Chiosis et al. |
| 2016/0264577 | A1 | 9/2016 | Sun et al. |
| 2016/0310497 | A1 | 10/2016 | Chiosis et al. |
| 2016/0333014 | A1 | 11/2016 | Chiosis |
| 2017/0151247 | A1 | 6/2017 | Taldone et al. |
| 2017/0342073 | A1 | 11/2017 | Chiosis et al. |

FOREIGN PATENT DOCUMENTS

| CA | 2 652 263 | A1 | 11/2007 |
| JP | 2005-519848 | A | 7/2005 |
| JP | 2008-531599 | A | 8/2008 |
| JP | 2009-542716 | A | 12/2009 |
| WO | 98/51702 | | 11/1998 |
| WO | 00/61578 | | 10/2000 |
| WO | 02/36075 | | 5/2002 |
| WO | WO 02094259 | A1 * | 11/2002 |
| WO | WO 03037860 | A2 * | 5/2003 |
| WO | WO-2005/000300 | A1 | 1/2005 |

(Continued)

OTHER PUBLICATIONS

Gallo, "Targeting Hsp90 to Halt Neurodegeneration", Chem.Bio., Feb. 2006, vol. 13, iss. 2, pp. 115-116.*

(Continued)

*Primary Examiner* — Jeffrey S Lundgren
*Assistant Examiner* — Stephanie K Springer
(74) *Attorney, Agent, or Firm* — Choate, Hall & Stewart LLP; Brenda Herschbach Jarrell; John P. Rearick

(57) ABSTRACT

Treatment of neurodegenerative diseases is achieved using small molecule purine scaffold compounds that inhibit Hsp90 and that possess the ability to cross the blood-brain barrier or are other wise delivered to the brain.

47 Claims, 16 Drawing Sheets

(56) References Cited

FOREIGN PATENT DOCUMENTS

| WO | 2005/012482 | 2/2005 |
| --- | --- | --- |
| WO | 2006/084030 | 8/2006 |
| WO | 2006/130469 | 12/2006 |
| WO | 2007/117466 | 10/2007 |
| WO | 2008/013985 | 1/2008 |
| WO | 2008/056120 | 5/2008 |
| WO | 2008/070472 | 6/2008 |
| WO | 2009/007399 | 1/2009 |
| WO | 2009/042646 | 4/2009 |
| WO | 2009/065035 | 5/2009 |
| WO | WO-2011/044394 A1 | 4/2011 |
| WO | WO-2012/138894 A1 | 10/2012 |
| WO | WO-2012/138896 A1 | 10/2012 |

OTHER PUBLICATIONS

He et al. "Identification of Potent Water Soluble Purine-Scaffold Inhibitors of the Heat Shock Protein 90", J Med Chem, 2006, vol. 49, pp. 381-390.*

Faassen et al. "Caco-2 permeability, P-glycoprotein transport ratios and brain penetration of heterocyclic drugs", Int.J.Pharmaceutics, 2003, vol. 263, pp. 113-122.*

Dragunow "The adult human brain in preclinical drug development", Nature Reviews Drug Discovery, 2008, vol. 7, pp. 659-666.*

Kakimura et al. "Microglial activation and amyloid-b clearance induced by exogenous heat-shock proteins", The FASEB Journal, 2002, vol. 16, pp. 601-603.*

Noorbakhsh et al. "Deciphering complex mechanisms in neurodegenerative diseases: the advent of systems biology", Trends in Neurosciences, 2009, vol. 32, issue 2, pp. 88-100.*

Silverman, The Organic Chemistry of Drug Design and Drug Action, 2nd ed., 2004, pp. 25-34.*

Patani et al. "Bioisosterism: A Rational Approach in Drug Design", Chem.Rev., 1996, vol. 96, pp. 3147-3176.*

Kawai et al. "Structure-activity relationship study of novel NR2B-selective antagonists with arylamides to avoid reactive metabolites formation", Bioorg.Med.Chem.Lett., 2007, vol. 17, pp. 5537-5542.*

Lee et al. "Tau phosphorylation in Alzheimer's disease: pathogen or protector?", Trends in Mol. Med., 2005, vol. 11, No. 4, pp. 164-169.*

Ahlijanian, Michael K. et al. "Hyperphosphorylated tau and neurofilament and cytoskeletal disruptions in mice overexpressing human p25, an activator of cdk5" PNAS, Mar. 14, 2000, pp. 2910-2915, vol. 97, No. 6.

Alvarez, Alejandra et al. "Inhibition of tau phosphorylating protein kinase cdk5 prevents β-amyloid-induced neuronal death" FEBS Letters, 1999, pp. 421-426, vol. 459.

Auluck, Pavin et al. "Pharmacological prevention of Parkinson disease in Drosophila", Nature Medicine, Nov. 2002, pp. 1185-1186, vol. 8, No. 11.

Brion, Jean-Piene et al. "Cortical and Brainstem-Type Lewy Bodies are Immunoreactive for the Cyclin-Dependent Kinase 5" American Journal of Pathology, Nov. 1995, pp. 1465-1476, vol. 147, No. 5.

Cadepond, Françoise et al. "Heat Shock Protein 90 as a Critical Factor in Maintaining Glucocorticosteroid Receptor in a Nonfunctional State", The Journal of Biological Chemistry, 1991, pp. 5834-5841, vol. 266, No. 9.

Chae, Teresa et al. "Mice Lacking p35, a Neuronal Specific Activator of Cdk 5, Display Cortical Lamination Defects, Seizures, and Adult Lethality", Neuron, Jan. 1997, pp. 29-42, vol. 18.

Chen, Jingshan et al. "Induction of Cyclin-Dependent Kinase 5 in the Hippocampus by Chronic Electroconvulsive Seizures: Role of ΔFosB", The Journal of Neuroscience, Dec. 15, 2000, pp. 8965-8971, vol. 20, No. 24.

Donźe, Olivier et al. "The Hsp90 chaperone complex is both a facilitator and a repressor of the dsRNA-dependent kinase PKR",The EMBO Journal, 2001, pp. 3771-3780, vol. 20, No. 14.

Dou, Fei et al. "Chaperones increase association of tau protein with microtubules", PNAS, Jan. 21, 2003, pp. 721-726, vol. 100, No. 2.

Fath, Thomas et al. "Tau0Mediated Cytotoxicity in a Pseudohyperphosphorylation Model of Alzheimer's Disease", The Journal of Neuroscience, Nov. 15, 2002, pp. 9733-9741, vol. 22, No. 22.

Greenberg, Sharon et al. "A preparation of Alzheimer paired helical filaments that displays distinct T proteins by polyacrylamide gel elecrophoresis", PNAS, Aug. 1990, pp. 5827-5831, vol. 87.

He, Huazhong et al. "Identification of Potent Water Soluble Purine-Scaffold Inhibitors of the Heat Shock Protein 90", J. Med. Chem., 2006, pp. 381-390, vol. 49.

Huezo, Henri et al. "Microtiter Cell-Based Assay for Detection of Agents that Alter Cellular Levels of Her2 and EGFR" Chemistry and Biology, 2003, pp. 629-634, vol. 10.

Lamphere, Lou et al. "Interaction between Cdc37 and Cdk4 in human cells", Oncogene, 1997, pp. 1999-2004, vol. 14.

Lazaro, Jean-Bernard et al. "Cyclin dependent kinase 5, cdk5, is a positive regulator of myogenesis in mouse C2 cells", Journal of Cell Science, 1997, pp. 1251-1260, vol. 110.

Lucas, José et al. "Decreased nuclear β -catenin, tau hyperphosphorylation and neurodegeneration in GSK-3β conditional transgenic mice", The EMBO Journal, 2001, pp. 27-39, vol. 20, No. 1 and 2.

Maccioni, Ricardo et al. "The protein kinase Cdk5", Euro. J. Biochem., 2001, pp. 1518-1527, vol. 268.

Matsumura, Nobutaka et al. "Stable Expression in Chinese Hamster Ovary Cells of Mutated TAU Genes Causing Frontotemporal Dementia and Parkinsonism Linked to Chromosome 17 (FTDP-17)", American Journal of Pathology, Jun. 1999, pp. 1649-1656, vol. 154, No. 6.

Neystat, Michael et al. "Expression of cyclin-dependent kinase 5 and its activator p35 in models of induced apoptotic death in neurons of the substantia nigra in vivo", Journal of Neurochemistry, 2001, pp. 1611-1625, vol. 77.

Noble, Wendy et al. "Cdk5 Is a Key Factor in TAU Aggregation and Tangle Formation In Vivo", Neuron, May 22, 2003, pp. 555-565, vol. 38.

Ohshima, Toshio et al. "Targeted disruption of the cyclin-dependent kinase 5 gene results in abnormal corticogenesis, neuronal pathology and perinatal death", PNAS, Oct. 1996, pp. 11173-11178, vol. 93.

Paudel, Hemant et al. "Brain Proline-directed Protein Kinase Phosphorylates Tau on Sites That are Abnormally Phosphorylated in Tau Associated with Alzheimer's Paired Helical Filaments", The Journal of Biological Chemistry, 1993, pp. 23512-23518, vol. 268, No. 31.

Sahara, Naruhiko et al. "Assembly of tau in transgenic animals expressing P301L tau: alteration of phosphorylation and solubility", Journal of Neurochemistry, 2002, pp. 1498-1508, vol. 83.

Sakaeda, Toshiyuki et al."Molecular and Pharmacokinetic Properties of 222 Commercially Available Oral Drugs in Humans", Biol. Pharm. Bull. 2001, pp. 935-940, vol. 24, No. 8.

Sittler, Annie et al. "Geldanamycin activated a heat shock response and inhibits huntingtin aggregation in a cell culture model of Huntington's Disease", Human Molecular Genetics, 2001, pp. 1307-1315, vol. 10, No. 12.

Stancato, Louis et al. "The hsp90-binding Antibiotic Geldanamycin Decreased Raf Levels and Epidermal Growth Factor Signaling without Disrupting Formation of Signaling Complexes or Reducing the Specific Enzymatic Activity of Raf Kinase", The Journal of Biological Chemistry, 1997, pp. 4013-4020, vol. 272, No. 7.

Tatebayashi, Yoshitaka et al. "Tau filament formation and associative memory deficit in aged mice expression mutant (R406W) human tau", PNAS, Oct. 15, 2002, pp. 13896-13901, vol. 99, No. 21.

Tatzelt, Jörg et al. "Scarpie prions selectively modify the stress response in neuroblastoma cells", PNAs, Mar. 1995, pp. 2944-2948, vol. 92.

Tsai, Ki-Huei et al. "Activity and expression pattern of cyclin-dependent kinase 5 in the embryonic mouse nervous system", Development, 1993, pp. 1029-1040, vol. 119.

(56) References Cited

OTHER PUBLICATIONS von Bergen, Martin et al. "Mutations of Tau Protein in Frontotemporal Dementia Promote Aggregation of Paired Helical Filaments by Enhancing Local β-Structure", The Journal of Biological Chemistry, 2001, pp. 48165-48174, vol. 276, No. 51.
Waza, Mashiro et al. "17-AAG, an Hsp90 inhibitor, ameliorates polyglutamine-mediated motor neuron degeneration", Nature Medicine, Oct. 2005, pp. 1088-1095, vol. 11, No. 10.
Winklhofer, Konstanze et al. "Geldanamycin Restores a Defective Heat Shock Protein Response in Vivo", The Journal of Biological Chemistry, 2001, pp. 45160-45167, vol. 276, No. 48.
Zou, Jiangying et al. "Repression of Heat Shock Transcription Factor HSF1 Activation by HSP90 (HSP90 Complex) that Forms a Stress-Sensitive Complex with HSF1", Cell, 1998, pp. 471-480, vol. 94.
Dickey, C. et al. "Development of a High Throughput Drug Screening Assay for the Detection of Changes in Tau Levels—Proof of Concept with HSP90 inhibitors" Current Alzheimer Research, 2005, pp. 231-238, vol. 2, No. 2.
Dickey, C. et al. "The high-affinity HSP90-CHIP complex recognizes and selectively degrades phosphorylated tau client proteins" The Journal of Clinical Investigation, Mar. 2007, pp. 648-658, vol. 117, No. 3.
Kamal, A. et al. "Small-molecule HSP90 Inhibitors: Applications in Cancer and Neurodegenerative Diseases" Heat Shock Proteins in Cancer, 2007, pp. 275-294, Chapter 14, vol. 2.
Luo, W. et al. "Heat shock protein 90: translation from cancer to Alzheimer's disease treatment" BMC Neuroscience, Dec. 3, 2008, pp. 18, vol. 9.
Luo, W. et al. "Roles of heat-shock protein 90 in maintaining and facilitating the neurodegenerative phenotype in tauopathies" PNAS, May 29, 2007, pp. 9511-9516, vol. 104, No. 22.
Soti, C. et al. "Heat shock proteins as emerging therapeutic targets", British Journal of Pharmacology, 2005, pp. 769-780, vol. 146.
Shen, Hai-Ing et al. "Geldanamycin Induces Heat Shock Protein 70 and Protects against MPTP-induced Dopaminergic Neurotoxicity in Mice" The Journal of Biological Chemistry, 2005, pp. 39962-39969, vol. 280, No. 48.
Waza, Masahiro et al. "Alleviating Neurodegeneration by an Anticancer Agent an Hsp90 Inhibitor (17-AAG)", Department of Neurology, 2006, pp. 21-24.
Katsuno, Masahisa et al., Spinal and bulbar muscular atrophy, Advances in Neurological Sciences, 2005, vol. 49, No. 6, pp. 891-897.
Beebe, K. et al., Posttranslational modification and conformational state of heat shock protein 90 differentially affect binding of chemically diverse small molecule inhibitors, Oncotarget, 4(7):1065-74 (2013).
Extended European Search Report for EP 07812557.2, 10 pages (dated Jul. 27, 2012).
Huang, Y. et al., Chemogenomic analysis identifies geldanamycins as substrates and inhibitors of ABCB1, Pharm. Res., 24(9):1702-12 (2007).
International Search Report for PCT/US2007/072671, 1 page (dated Sep. 12, 2008).
King, F.D. Bioisosteres, Conformational Restrictions, and Prodrugs—Case History: An Example of a Conformational Restriction Approach, Chapter 14, Med. Chem: Principle and Practice, pp. 206-209 (1994).
Schulte, T.W. and Neckers, L.M., The benzoquinone ansamycin 17-allylamino-17-demethoxygeldanamycin binds to HSP90 and shares important biologic activities with geldanamycin, Cancer. Chemother. Pharmacol., 42(4):273-9 (1998).
Written Opinion for PCT/US2007/072671, 6 pages (dated Sep. 12, 2008).
Zhao, H. et al., Hsp90 modulation for the treatment of Alzheimer's disease, Adv. Pharmacol., 64:1-25 (2012).

Abraham, M.H. et al., Hydrogen bonding part 46: a review of the correlation and prediction of transport properties by an LFER method: physicochemical properties brain penetration and skin permeability, Pesticides Science, 55:78-88 (1999).
Auluck, P.K. et al., Chaperone suppression of alpha-synuclein toxicity in a Drosophila model for Parkinson's disease, Science, 295(5556):865-8 (2002).
Author Not Known, Ministry of Health and Welfare, study for overcoming refractory diseases, team for studying ataxia, general overview report in 2005, Mar. 31, 2006, p. 69-71.
Author Not Known, Study for controlling and preventing of aging by utilizing stress-response function derived from the living organism, general overview report in 2005, Mar. 2006, p. 1-8.
Bajaj, N.P. et al., Cyclin-dependent kinase-5 is associated with lipofuscin in motor neurones in amyotrophic lateral sclerosis, Neuroscience Letters, 245(1):45-48 (1998).
Barral, J.M. et al., Roles of molecular chaperones in protein misfolding diseases, Seminars in Cell and Development Biology, 15(1):17-29 (2004).
Beglopoulos, V. and Shen, J., Regulation of CRE-dependent transcription by presenilins: prospects for therapy of Alzheimer's disease, Trends in Pharmacological Sciences, 27(1):33-40 (2006).
Bibb, J.A. et al., Effects of chronic exposure to cocaine are regulated by the neuronal protein Cdk5, Nature, 410(6826):376-380 (2001).
Clark, D.E., In silico prediction of blood-brain barrier permeation, Drug Discovery Today, 8(20):927-933 (2003).
Ertl, P. et al., Fast calculation of molecular polar surface area as a sum of fragment-based contributions and its application to the prediction of drug transport properties, Journal of Medicinal Chemistry, 43:3714-3717 (2000).
Evans, C.G. et al., Heat shock proteins 70 and 90 inhibit early stages of amyloid beta-(1-42) aggregation in vitro, J. Biol. Chem., 281(44):33182-33191 (2006).
Fahn, S., Description of Parkinson's disease as a clinical syndrome, Annals of the New York Academy of Sciences, 991:1-14 (2003).
Feng, M.R., Assessment of blood-brain penetration: in silico, in vitro and in vivo, Current Drug Metabolism, 3(6):647-657 (2002).
Ferrer, I., et al., Current advances on different kinases involved in tau phosphorylation, and implications in Alzheimer's disease and tauopathies, Current Alzheimer Research, 2(1):3-18 (2005).
Flower, T.R. et al., Heat shock prevents alpha-synuclein-induced apoptosis in a yeast model of Parkinson's disease, J. Mol. Biol., 351(5):1081-100 (2005).
Fu, W.Y. et al., Induction of Cdk5 activity in rat skeletal muscle after nerve injury, Neuroreport, 13(2):243-247 (2002).
Green, S.L. et al., Alterations in cyclin-dependent protein kinase 5 (CDK5) protein levels, activity and immunocytochemistry in canine motor neuron disease, Journal of Neuropathology and Experimental Neurology, 57(11):1070-1077 (1998).
Gárdián, G. and Vécsei, L., Huntington's disease: pathomechanism and therapeutic perspectives, Journal of Neural Transmission, 111(10-11):1485-1494 (2004).
Götz, J. et al., Formation of neurofibrillary tangles in P301l tau transgenic mice induced by Abeta 42 fibrils, Science, 293(5534):1491-1495 (2001).
Hansch, C. et al., Hydrophobicity and central nervous system agents: on the principle of minimal hydrophobicity in drug design, J. Pharm. Sci., 76(9):663-87 (1987).
He, H. et al., General method for the synthesis of 8-arylsulfanyl adenine derivatives, The Journal of Organic Chemistry, 69(9):3230-3232 (2004).
Hong, M. et al., Tau-based neurofibrillary lesions, Neurodegenerative dementia: Clinical features and pathological mechanisms, Clark, C.M. And Trojanowski, J.Q., eds., New York: McGraw-Hill, 161-175 (2000).
Honjyo, Y. et al., P39 immunoreactivity in glial cytoplasmic inclusions in brains with multiple system atrophy, Acta Neuropathologica, 101(3):190-194 (2001).
Huang, C. et al., Heat shock protein 70 inhibits alpha-synuclein fibril formation via interactions with diverse intermediates, J. Mol. Biol., 364(3):323-36 (2006).

(56) References Cited

OTHER PUBLICATIONS

Hutton, M. et al., Association of missense and 5'-splice-site mutations in tau with the inherited dementia FTDP-17, Nature, 393(6686):702-705 (1998).

Julien, J.P. and Beaulieu, J.M., Cytoskeletal abnormalities in amyotrophic lateral sclerosis: beneficial or detrimental effects, Journal of Neurological Sciences, 180(1-2):7-14 (2000).

Julien, J.P. et al., Transgenic mice in the study of ALS: the role of neurofilaments, Brain Pathology, 8(4):759-769 (1998).

Kanemaru, K. et al., Fetal-type phosphorylation or the tau in paired helical filaments, Journal of Neurochemistry, 58(5):1667-1675 (1992).

Katsuno, M. et al., Pharmacological induction of heat-shock proteins alleviates polyglutamine-mediated motor neuron disease, Proc. Natl. Acad. Sci. U S A, 102(46):16801-6 (2005).

Kelder, J. et al., Polar molecular surface as a dominating determinant for oral absorption and brain penetration of drugs, Pharmaceutical Research, 16(10):1514-1519 (1999).

Kim, J. et al., Development or a fluorescence polarization assay for the molecular chaperone Hsp90, Journal of Biomolecular Screening, 9(5):375-381 (2004).

Klettner, A., The induction of heat shock proteins as a potential strategy to treat neurodegenerative disorders, Drug News and Perspectives, 17(5):299-306 (2004).

Lee, K.Y. et al., Elevated neuronal Cdc2-like kinase activity in the Alzheimer disease brain, Neuroscience Research, 34(1):21-29 (1999).

Lee, V. M. et al., Neurodegenerative tauopathies, Annual Review of Neuroscience, 24:1121-1159 (2001).

Lewis, J. et al., Enhanced neurofibrillary degeneration in transgenic mice expressing mutant tau and APP, Science, 293(5534):1487-1491 (2001).

Lewis, J. et al., Neurofibrillary tangles, amyotrophy and progressive motor disturbance in mice expressing mutant (P301 L) tau protein, Nature Genetics, 25(4):402-405 (2000).

Lin, J.H. Rodrigues, A.D., In vitro model for early studies of drug metabolism, In: Pharmacokinetics optimization in drug research: biological, physicochemical and computational strategies, 217-243 (2001).

Lipinski, C.A. et al., Experimental and computational approaches to estimate solubility and permeability in drug discovery and development settings, Advanced Drug Delivery Reviews, 23(1-3): 3-26 (2001).

Llauger, L. et al., Synthesis of novel fluorescent probes for the molecular chaperone Hsp90, Bioorganic and Medicinal Chemistry Letters, 13(22):3975-3978 (2003).

Mandelkow, E. and Mandelkow, E.M., Kinesin motors and disease, Trends in Cell Biology, 12(12):585-591 (2002).

Michel, G. et al., Characterization of tau phosphorylation in glycogen synthase kinase-3beta and cyclin dependent kinase-5 activator (p23) transfected cells, Biochimica et Biophysica Acta, 1380(2):177-182 (1998).

Morimoto, R.I. and Santoro, M.G., Stress-inducible responses and heat shock proteins.

Moulick, K. et al., Synthesis of a red-shifted fluorescence polarization probe for Hsp90, Bioorganic and Medicinal Chemistry Letters, 16(17):4515-4518 (2006).

Nakamura, S. et al., Cyclin-dependent kinase 5 and mitogen-activated protein kinase in glial cytoplasmic inclusions in multiple system atrophy, Journal of Neuropathology and Experimental Neurology, 57(7):690-698 (1998).

Nakamura, S. et al., Cyclin-dependent kinase 5 in Lewy body-like inclusions in anterior horn cells of a patient with sporadic amyotrophic lateral sclerosis, Neurology, 48(1):267-270 (1997).

Nakano, S. et al., Aberrant expression of cyclin-dependent kinase 5 in inclusion body myositis, Neurology, 53(8):1671-1676 (1999).

Osterberg, T. and Norinder, U., Prediction of polar surface area and drug transport processes using simple parameters and PLS statistics, Journal of Chemical Information and Computer Science, 40(6):1408-1411 (2000).

Patrick, G.N. et al., Conversion of p35 to p25 deregulates Cdk5 activity and promotes neurodegeneration, Nature, 402(6762):615-622 (1999).

Poletti, A. et al., Reflections on the diseases linked to mutations of the androgen receptor, Endocrine, 28(3):243-262 (2005).

Poorkaj, P. et al., Tau is a candidate gene for chromosome 17 frontotemporal dementia, Annals of Neurology, 43(6):815-825 (1998).

Rajgopal, Y. and Vemuri, M.C., Ethanol induced changes in cyclin-dependent kinase-5 activity and its activators, P35, P67 (Munc-18) in rat brain, Neuroscience Letters, 308(3):173176 (2001).

Sisodiya, S.M. et al., Abnormal expression of cdk5 in focal cortical dysplasia in humans, Neuroscience Letters, 328(3):217-220 (2002).

Skaaeda, T. et al., Molecular and pharmacokinetic properties of 222 commercially available oral drugs in humans, Biological and Pharmaceutical Bulletin, 24(8):935-940 (2001).

Sorger, P.K., Heat shock factor and the heat shock response, Cell, 65(3):363-366 (1991).

Stoothoff, W.H. And Johnson, G.V., Tau phosphorylation: physiological and pathological consequences, Biochimica et Biophysica Acta, 1739(2-3):280-297 (2005).

Söti, C. and Csermely, P., Chaperones and aging: role in neurodegeneration and in other civilizational diseases, Neurochemistry International, 41(6):383-389 (2002).

Van De Waterbeemd, H. et al., Estimation of blood-brain barrier crossing of drugs using molecular size and shape, and H-bonding characteristics, Journal of Drug Targeting, 6(2):151-165 (1998).

Veber, D.F. et al., Molecular properties that influence the oral bioavailability of drug candidates, Journal of Medicinal Chemistry, 45(12):2615-2623 (2002).

Walling, A.D., Amyotrophic lateral sclerosis: Lou Gehrig's disease, American Family Physician, 59(6):1489-1496 (1999).

Wang, J. et al., Cdk5 activation induces hippocampal CA1 cell death by directly phosphorylating NMDA receptors, Nature Neuroscience, 6(10):1039-1047 (2003).

Weishaupt, J.H. et al., Inhibition of CDK5 is protective in necrotic and apoptotic paradigms of neuronal cell death and prevents mitochondrial dysfunction, Molecular and Cellular Neuroscience, 24(2):489-502 (2003).

Xu, H. et al., Estrogen reduces neuronal generation of Alzheimer beta-amyloid peptides, Nature Medicine, 4(4):447-451 (1998).

\* cited by examiner

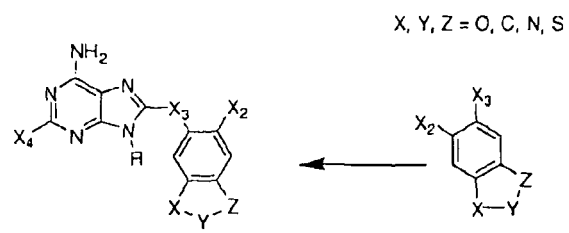
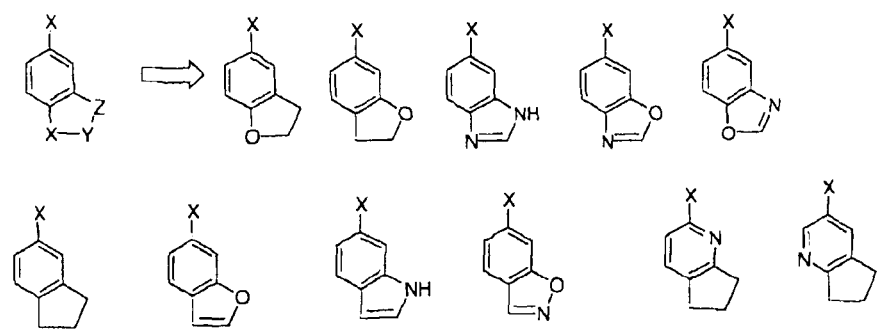
benzofurans, 2,3-dihydrobenzofurans, indoles, beinisoxazoles, benoxazoles, benzimidazoles
2,3-Cyclopentenopyridines, benzothiophen-3(2H)ones, benzothiophene
Fig. 4

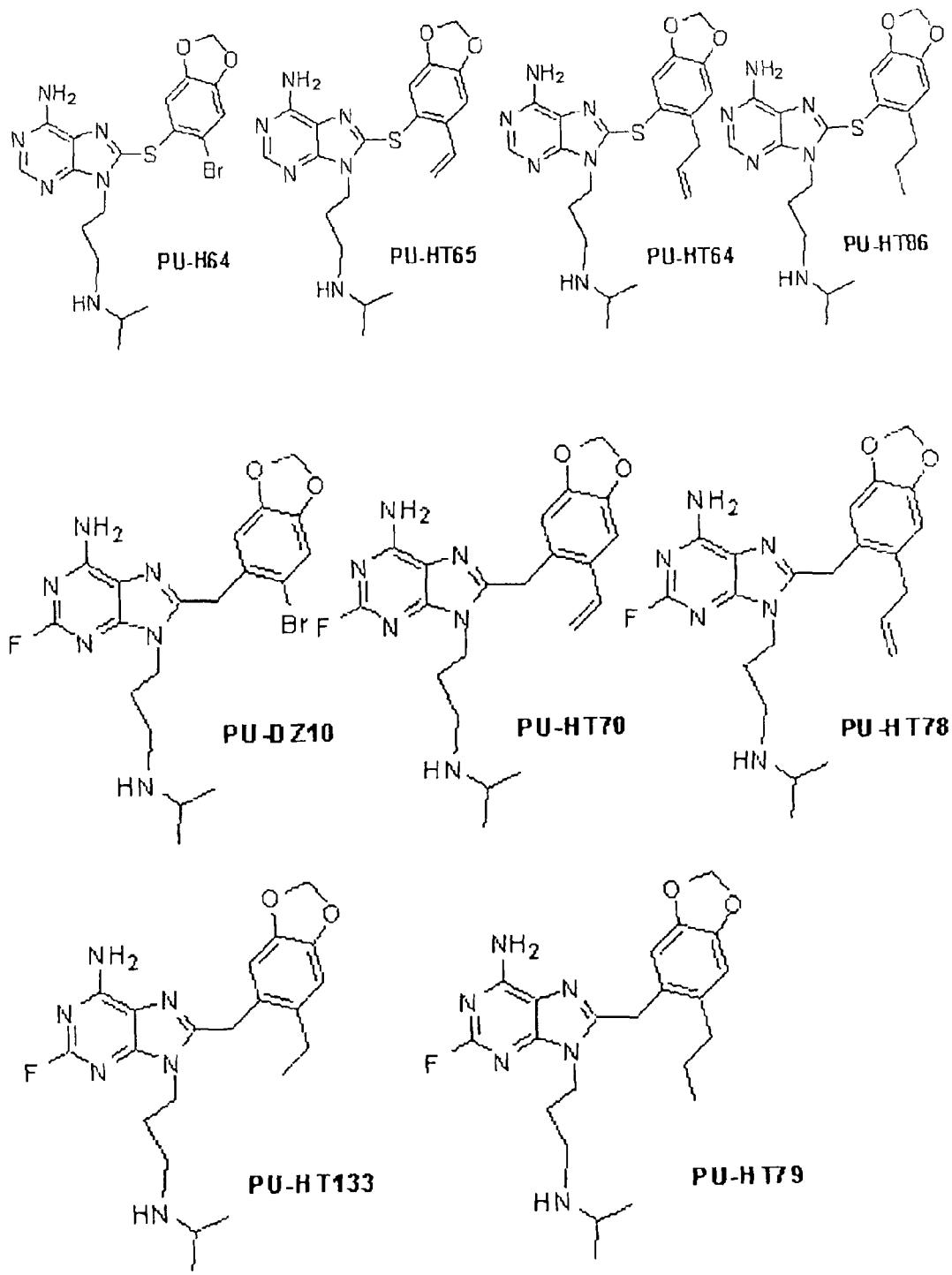
Fig. 5, Part 1

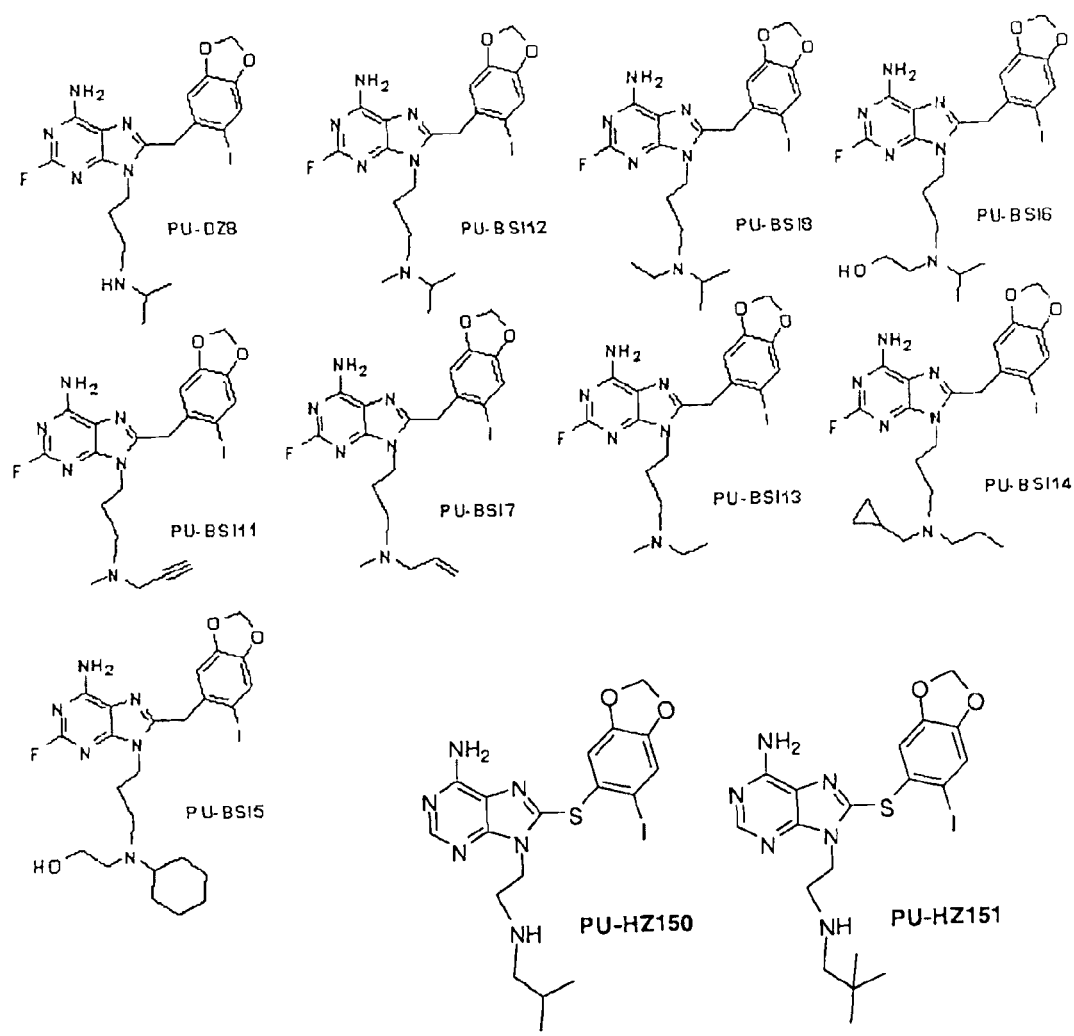
Fig. 5, part 2

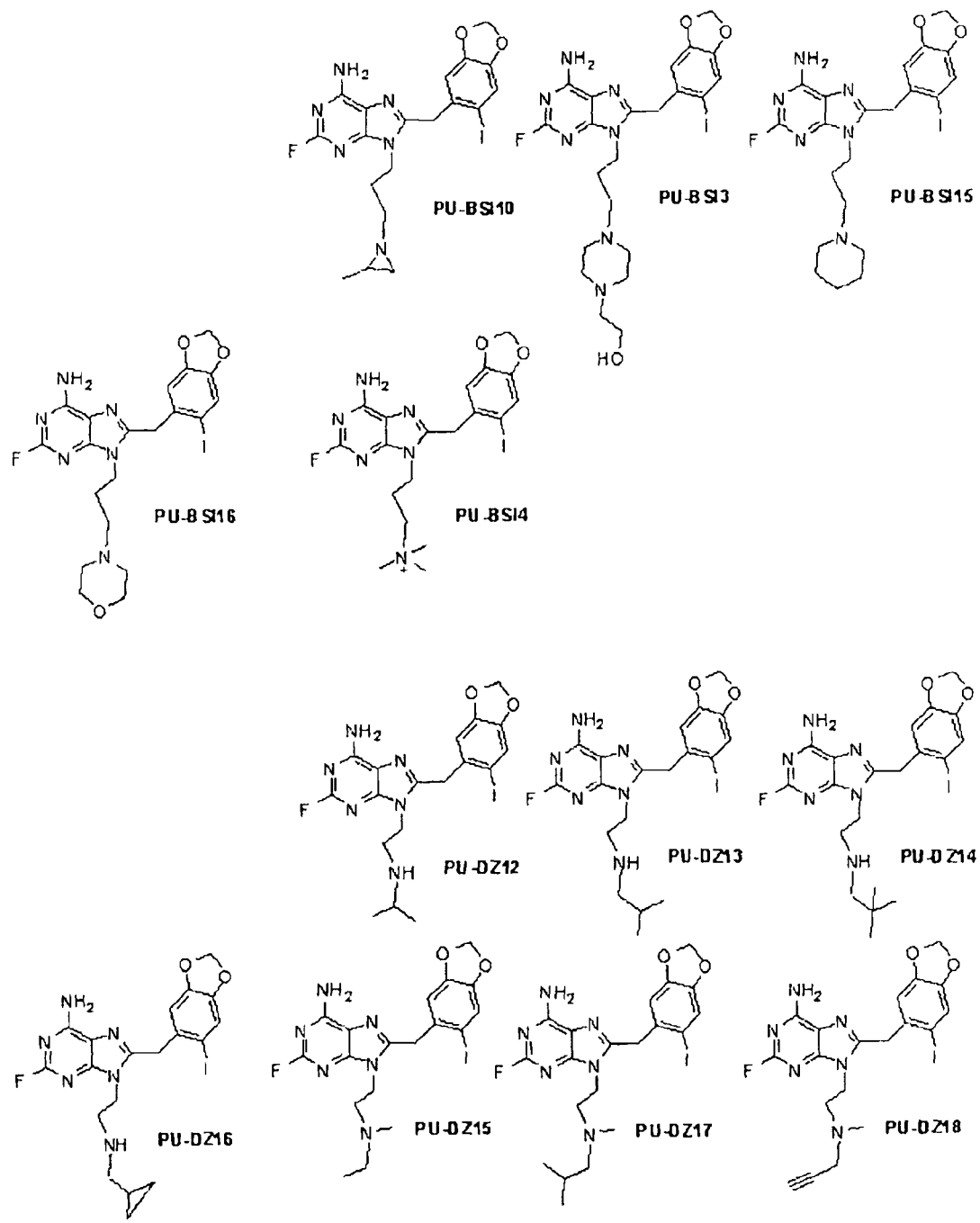
Fig. 5, Part 3

Reagents and conditions: (a) K2CO3, DMAP, DMF, 120°C; (b) NaOMe, MeOH, i-BuOH, 105°C; (c) HF-pyridine, NaNO2, rt; (d) NBS, DMF, rt or NIS, CF3COOH, DMF, rt; (e) Cs2CO3, DMF, 50°C.

Reagents and conditions: (a) NaOt-Bu, neocuproine, CuI, DMF, 110°C; (b) NIS, CF3COOH, acetonitrile, rt.

TREATMENT OF NEURODEGENERATIVE DISEASES THROUGH INHIBITION OF HSP90

CLAIM FOR PRIORITY

This application claims the priority benefit of U.S. Provisional Application No. 60/806,427, filed Jun. 30, 2006, which is incorporated herein by reference for all purposes.

STATEMENT OF FEDERAL FUNDING

This invention was supported in part by NIH grant AG09464. The United States government may have certain rights in this invention.

JOINT RESEARCH AGREEMENT

This invention was made pursuant to a joint research agreement between inventors with an obligation to assign their invention to Sloan-Kettering Institute for Cancer Research and inventors with an obligation to assign their invention to Rockefeller University. This joint research agreement was in effect at the time the invention claimed in this application was made.

BACKGROUND OF THE INVENTION

This application relates to the treatment of neurodegenerative diseases through inhibition of heat shock protein 90 (HSP90).

The HSP90 family of proteins has four recognized members in mammalian cells: Hsp90α and β, Grp94 and Trap-1. Hsp90α and β exist in the cytosol and the nucleus in association with a number of other proteins. Hsp90 in its various forms is the most abundant cellular chaperone, and has been shown in experimental systems to be required for ATP-dependent refolding of denatured or "unfolded" proteins. It has therefore been proposed to function as part of the cellular defense against stress. When cells are exposed to heat or other environmental stresses, the aggregation of unfolded proteins is prevented by pathways that catalyze their refolding or degradation. This process depends on the association of the unfolded protein in an ordered fashion with multiple chaperones (Hsp 60, 90 and 70 and p23), forming a "refoldosome" and ultimately the ATP-dependent release of the chaperones from the refolded protein.

Hsp90 may also play a role in maintaining the stability and function of mutated proteins. It seems to be required for expression of mutated p53 and v-src to a much greater extent than for their wild-type counterparts. It has been suggested that this occurs as a result of Hsp90-mediated suppression of the phenotypes of mutations that lead to protein unfolding.

Hsp90 is also necessary to the conformational maturation of several key proteins involved in the growth response of the cell to extracellular factors. These include the steroid receptors as well as certain transmembrane kinases (i.e., Raf serine kinase, v-src and Her2). The mechanism whereby Hsp90 affects these proteins is not fully understood, but appears to be similar to its role in protein refolding. In the case of the progesterone receptor, it has been shown that binding and release of Hsp90 from the receptor occurs in a cyclic fashion in concert with release of other chaperones and immunophilins and is required for high affinity binding of the steroid to the receptor. Thus, Hsp90 could function as a physiologic regulator of signaling pathways, even in the absence of stress.

Hsp90 has been shown to be overexpressed in multiple tumor types and as a function of oncogenic transformation. Whether it plays a necessary role in maintaining transformation is unknown, but it could have at least three functions in this regard. Cancer cells grow in an environment of hypoxia, low pH and low nutrient concentration. They also rapidly adapt to or are selected to become resistant to radiation and cytotoxic chemotherapeutic agents. Thus, the general role of Hsp90 in maintaining the stability of proteins under stress may be necessary for cell viability under these conditions. Secondly, cancer cells harbor mutated oncogenic proteins. Some of these are gain-of-function mutations which are necessary for the transformed phenotype. Hsp90 may be required for maintaining the folded, functionally-active conformation of these proteins. Thirdly, activation of signaling pathways mediated by steroid receptors, Raf and other Hsp90 targets is necessary for the growth and survival of many tumors which thus probably also require functional Hsp90.

Neurodegeneration, similar to cancer, is likely not the result of a single dysregulatory event, but rather a several-step process involving environmental, epigenetic and genetic events that lead to creation of a complex transformed phenotype manifested by abnormal expression, post-translational modification and processing of certain proteins. The functional maintenance of these dysregulated proteins in neurons may require, analogously to the cancer afflicted cell, the regulatory mechanism of molecular chaperones to evolve along with the transforming process.

In the context of neurodegenerative diseases, Hsp90 may play two roles. First, aberrantly activated kinases (such as cdk5/p35, gsk3beta) in neurodegenerative diseases may require Hsp90 for functioning. Thus, Hsp90 inhibition may restore damaged signaling networks in the diseased brain by alleviating aberrant phosphorylation, leading to reduced aberrant protein aggregation, and elimination or reduction of aggregates and of their associated toxicity. Second, pathogenic mutants (such as of APP or presenilins in AD or mtau in FTDP-17 or mutant androgen receptor in bulbar muscular atrophy) may require Hsp90 for correct folding and functioning, thus Hsp90 inhibition may lead to the elimination of these proteins and result in reduction of aggregates and consequent plaque or tangle formation.

Most neurodegenerative diseases are probably characterized by both mutants and aberrant signaling, and Hsp90 can play a role with respect to pathogenic mutants as well. Tau mutations cause autosomal dominant frontal temporal dementia. Pathologies linked to mutations of the androgen receptor include the complete androgen insensitivity syndrome (CAIS) and the spinal and bulbar muscular atrophy (SBMA or Kennedy's disease). (4) Mutations in the presenilin genes are the major cause of familial AD. Analysis of conditional knockout mice has shown that inactivation of presenilins results in progressive memory impairment and age-dependent neurodegeneration, suggesting that reduced presenilin activity might represent an important pathogenic mechanism. Presenilins positively regulate the transcription of cAMP response element (CRE)-containing genes, some of which are known to be important for memory formation and neuronal survival. (5) Alzheimer's Disease (AD) is characterized both by NFTs (tau aggregates) and plaques (Aβ deposits). In Alzheimer's disease, mutations in amyloid precursor protein or in the presenilins cause autosomal dominant disease. These are the substrate and proteases responsible for the production of the deposited peptide A. Prion mutations cause Gerstmann Straussler syndrome and hereditary Creutzfeldt-Jakob disease, alpha-synuclein mutations cause autosomal dominant Parkinson's disease. In these cases, the pathogenic mutation is in the protein that is deposited in the diseased tissue and the whole protein is deposited. Huntington D results from a mutant huntingtin. (9) Thus, in all the cases, the mutations lead to the disease by a mechanism that involves the deposition process.

These characteristics of Hsp90 make it a viable target for therapeutic agents. HSP90 family members possess a unique pocket in their N-terminal region that is specific to and conserved among all Hsp90s from bacteria to mammals, but which is not present in other molecular chaperones. The endogenous ligand for this pocket is not known, but it binds ATP and ADP with low affinity and has weak ATPase activity. The ansamycin antibiotics geldanamycin (GM) and herbimycin (HA) have been shown to bind to this conserved pocket, and this binding affinity has been shown for all members of the HSP90 family. International Patent Publication No. WO98/51702 discloses the use of ansamycin antibiotics coupled to a targeting moiety to provide targeted delivery of the ansamycin leading to the degradation of proteins in and death of the targeted cells. International Patent Publication No. WO00/61578 relates to bifunctional molecules having two moieties which interact with the chaperone protein Hsp96, including in particular homo- and heterodimers of ansamycin antibiotics. These bifunctional molecules act to promote degradation and/or inhibition of HER-family tyrosine kinases and are effective for treatment of cancers which overexpress Her-kinases.

Exemplary small molecule therapeutics that bind to the same binding pocket of Hsp90 as ATP and the ansamycin antibiotics are disclosed in PCT Publication No. WO02/36075, PCT Application No. PCT/US06/03676 and US Patent Publications 2005-0113339, 2005-0004026, 2005-0049263, 2005-0256183, 2005-0119292, 2005-0113340 and 2005-0107343, all of which are incorporated herein by reference.

In aged organisms, chaperone overload leads to a significant decrease in the robustness of cellular networks shifting their function towards a more stochastic behavior. Unbalanced chaperone requirement and chaperone capacity helps the accumulation of misfolded and aggregated proteins especially in the nervous system, due to the very limited proliferation potential of neurons. In addition, damaged signaling networks lose their original stringency, and irregular protein phosphorylation occurs. An appealing approach to alleviating and reversing such damaging effects is by modulating Hsp90 activity Inhibitors of Hsp90 activity release HSF1 from Hsp90 complexes and correct the defective regulation of HSF1 activity after heat stress leading to an increase in cellular levels of chaperones, such as Hsp70 and Hsp40. Overexpression of these chaperones has been shown to represent a general way of reinstating proper folding and alleviating misfolded proteins' toxic effects. In addition to their effects on reinstating correct folding, Hsp90 inhibitors may regulate proteins involved in signaling networks of diseased neurons.

The usefulness of Hsp90 inhibitors as clinical agents in the treatment of neurodegenerative diseases, however, will depend on whether their effects occur at concentrations of drug that are tolerable to the patient and on whether the drugs can be administered in such a fashion so as to achieve these concentrations in the brain. Unfortunately, known Hsp90 inhibitors such as geldanamycin and 17AAG, its derivative in Phase I clinical trial for cancer, and the unrelated compound radicicol have significant limitations. They are poorly soluble, difficult to formulate and do not cross the blood-brain barrier. Thus, in order to realize the potential for treatment of neurodegenerative diseases, therapeutic agents that inhibit Hsp90, and that have sufficient solubility and the ability to cross the blood-brain barrier or otherwise be delivered to the brain are needed.

SUMMARY OF THE INVENTION

In accordance with the present invention, treatment of neurodegenerative diseases is achieved using small molecule purine scaffold compounds that inhibit Hsp90 and that possess the ability to cross the blood-brain barrier. Thus, in accordance with the present invention, there is provided a method for treatment of neurodegenerative disease comprising the step of administering to an individual in need of such treatment an effective amount of a purine-scaffold compound that inhibits Hsp90, and that crosses the blood-brain barrier or is otherwise delivered to the brain.

In one embodiment, the purine scaffold compound used in the method of the invention has a purine moiety connected at the 8- or 9-position via a linker to a monocyclic substituent group. Such compounds are described in PCT Publication No. WO02/36075, PCT Application No. PCT/US06/03676 and US Patent Publications 2005-0113339, 2005-0004026, 2005-0049263, 2005-0256183, 2005-0119292, 2005-0113340 and 2005-0107343. In specific embodiments, the additional aryl or heteroaryl ring is affixed at the 9-position and is substituted at the 4' and 5' positions only.

In one embodiment, the method of the invention makes use of a small molecule purine scaffold compound has the general structure:

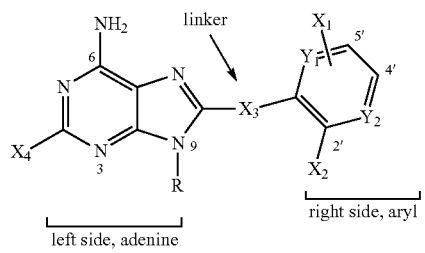

wherein R is hydrogen, a $C_1$ to $C_{10}$ alkyl, alkenyl, alkynyl, or an alkoxyalkyl group, optionally including heteroatoms such as N or O, optionally connected to the 2'-position to form an 8 to 10 member ring;

$Y_1$ and $Y_2$ are independently C, N, S or O, with the proviso that when $Y_1$ and/or $Y_2$ is O the double bonds are missing or rearranged to retain the aryl nature of the ring $X_4$ is hydrogen, halogen, for example F or Cl, or Br;

$X_3$ is $CH_2$, $CF_2$; 5, SO, $SO_2$, O, NH, or $NR^2$, wherein $R^2$ is alkyl; and $X_2$ is halogen, alkyl, halogenated alkyl, alkoxy, halogenated alkoxy, hydroxyalkyl, pyrollyl, optionally substituted aryloxy, alkylamino, dialkylamino, carbamyl, amido, alkylamido dialkylamido, acylamino, alkylsulfonylamido, trihalomethoxy, trihalocarbon, thioalkyl, $SO_2$— alkyl, COO-alkyl, $NH_2$, OH, or CN or part of a ring formed by R; and $X_1$ represents one more substituents on the aryl group, with the proviso that $X_1$ represents at least one substituent in the 5'-position said substituent in the 5'-position being selected from the same choices as $X_2$; $C_1$ to $C_6$ alkyl or alkoxy; or wherein $X_1$ has the formula —O—$(CH_2)$—O—, wherein n is 1 or 2, and one of the oxygens is bonded at the 5'-position of the aryl ring and the other is bonded to the 4' position.

The purine scaffold compound may be in the form of a salt, for example a hydrochloric or phosphoric acid salt to enhance solubility. (2)

The ride-side aryl group may be phenyl, or may include one or more heteroatoms. For example, the right-side aryl group may be a nitrogen-containing aromatic heterocycle such as pyrimidine.

In specific embodiments of the composition of the invention, the right-side aryl group is substituted at the 2' and 5' position only. In other embodiment, the right side aryl group is substituted at the 2', 4', and 5' positions. In yet other embodiments, the right side aryl group is substituted at the 4' and 5' positions only. As will be appreciated by persons skilled in the art, the numbering is based on the structure as drawn, and variations in the structure such as the insertion of a heteroatom may alter the numbering for purposes of formal nomenclature.

In other specific embodiments of the composition of the invention, the right side aryl group has a substituent at the 2'-position and $X_1$ has the formula —X—Y—Z— with X and Z connected at the 4' and 5' positions to the right side aryl, wherein X, Y and Z are independently C, N, S or O, connected by single or double bonds and with appropriate hydrogen, alkyl or other substitution to satisfy valence. In some embodiments, at least one of X, Y and Z is a carbon atom. In one specific embodiment, $X_1$ is —O—$(CH_2)_n$—O—, wherein n is 1 or 2, and one of the oxygen atoms is bonded at the 5'-position of the aryl ring and the other at the 4' position. Additional examples of compounds of this type are shown in the FIG. 4.

In accordance with specific embodiments of the invention, the purine scaffold composition has a formula as shown in FIG. 5.

The composition of the invention may also be a homodimer or heterodimer of these compounds in which a linker connects the right side aryl group of one moiety to the right side aryl group of another, or in which a linker connects the R group of one moiety to the R group of another provided that the compound retains the ability to inhibit hsp90 and also to cross the blood brain barrier.

BRIEF DESCRIPTION OF THE DRAWINGS

FIG. 4 shows compounds useful in the method of the invention.

FIG. 5 shows compounds useful in the method of the invention.

DETAILED DESCRIPTION OF THE INVENTION

Figure 1A:
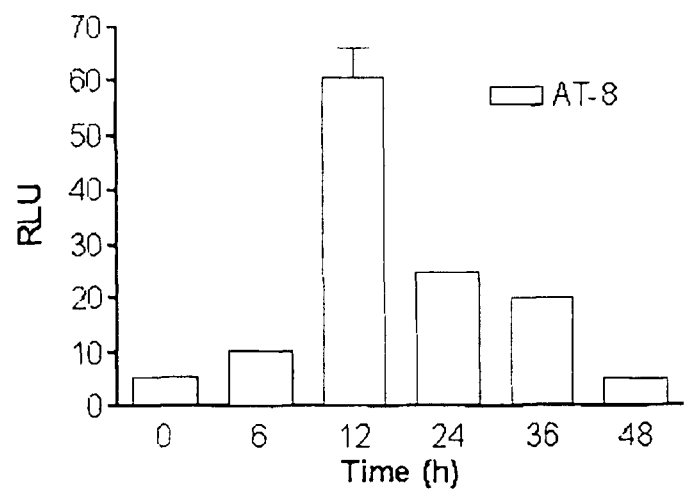
FIG. 1A shows tau phosphorylation activity in mouse brain following short term administration of PU24FC1.

The present invention provides a method for treatment of neurodegenerative disease, comprising the step of administering to an individual in need of such treatment a therapeutically effective amount of a purine scaffold compound that inhibits Hsp90 and that crosses the blood-brain barrier or is otherwise delivered to the brain.

As used in this application, the term "treatment" refers to delaying the onset of symptoms, reducing the severity or delaying the symptomatic progression of neurodegenerative disease in the individual. A cure of the disease is not required to fall within the scope of treatment. Further, it will be appreciated that the specific results of these treatment goals will vary from individual to individual, and that some individuals may obtain greater or lesser benefits than the statistical average for a representative population. Thus, treatment refers to administration of composition to an individual in need, with the expectation that they will obtain a therapeutic benefit.

The term "neurodegenerative disease" refers to disease characterized by abnormalities in signaling pathways, for example aberrant phosphorylation due to dysregulated kinase activity, mutant proteins (mutant tau, mutant APP) and chaperone unbalance leading to misfolding and increased apoptosis. In a specific embodiment, the neurodegenerative disease is a tauopathy, i.e. neurodegenerative disease characterized by tau protein abnormalities that share the feature of hyperphosphorylated tau protein, and intracellular neurofibrillary tangle (NFT) formation. Without limitation, the term "neurodegenerative diesease" as used in this application refers to and encompasses Alcohol-induced neurodegeneration (10)); Alzheimer's disease (11); Amyotrophic lateral sclerosis (13; 14); Brain ischemia (15; 20);

Cocaine addiction (21); Diffuse Lewy body disease (22); Electroconvulsive seizures (23); Fetal alcohol syndrome (10); Focal cortical dysplasia (24); Hereditary canine spinal muscular atrophy (25); Inclusion body myositis (26); Multiple system atrophy (27; 28); Niemann-Pick type C; Parkinson's disease (22); and Peripheral nerve injury (71).

The term "administering" refers to the act of introducing into the individual the therapeutic compound. In general, any route of administration can be used. Because the compounds used in the method of the invention may be capable of crossing the blood-brain barrier, systemic administration can be used. Thus, in certain embodiment of the invention, administration by oral, intravenous, intramuscular or parenteral injection is appropriate. Administration may also be done to the brain by inhalation because there is a compartment at the upper side of the nose that connects with the brain without having the BBB capillaries. Compounds that cross the blood brain barrier are preferred for this mode of administration as well, although this characteristics is not strictly required.

The term "therapeutically effective amount" encompasses both the amount of the compound administered and the schedule of administration that on a statistical basis obtains the result of preventing, reducing the severity or delaying the progression of neurodegenerative disease in the individual. As will be appreciated, preferred amounts will vary from compound to compound in order to balance toxicity/tolerance with therapeutic efficacy and the mode of administration. Determination of maximum tolerated dose and of the treatment regime in terms of number and frequency of dosing is a routine part of early clinical evaluation of a compound.

The term "crosses the blood brain barrier" as used herein refers to the ability of the compound to transit to the brain in detectable amounts following systemic administration. The ability of a compound to cross the blood brain barrier can be assessed using animal models such as mice As illustrated in the examples below, a single dose administration, for example at 50 to 200 mg/kg, can be employed, with animals sacrificed at intervals and the brain concentration of the compound determined. It will be appreciated that the extent to which a compound does transit to the brain will also have an impact on the amount of the therapeutic compound that is necessary. In general, however, compounds that cross the blood brain barrier will have molecular weights of less than 400 daltons, a degree of lipid solubility, preferably comparable to the compounds disclosed herein, the absence of restrictive plasma protein bindings and the absence of significant affinity for any of the several BBB active efflux transporters such as p-glycoprotein. In this regard, it is noted that 17-AAG does not effectively cross the blood brain barrier and is a P-glycoprotein substrate.

The therapeutic compound employed in the method of the present invention is suitably a small molecule purine scaffold compounds that inhibit Hsp90 and that possess the ability to cross the blood-brain barrier. The term "purine scaffold compound" refers to a compound that has a purine moiety that to which is bonded an additional aryl or heteroaryl ring at the 8- or 9-position, wherein the compound as a whole possesses the necessary flexibility and substituent groups to be received within the N-terminal pocket of Hsp90. These general requirements are discussed in PCT Publication No. WO02/36075.

In one embodiment, the method of the invention makes use of a small molecule purine scaffold compound has the general structure:

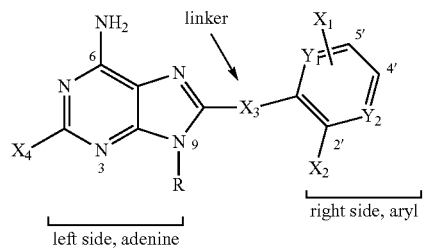

wherein R is hydrogen, a $C_1$ to $C_{10}$ alkyl, alkenyl, alkynyl, or an alkoxyalkyl group, optionally including heteroatoms such as N or O, optionally connected to the 2'-position to form an 8 to 10 member ring, $Y_1$ and $Y_2$ are independently C, N, S or O, with the proviso that when $Y_1$ and/or $Y_2$ is O the double bonds are missing or rearranged to retain the aryl nature of the ring $X_4$ is hydrogen, halogen, for example F or Cl, or Br;

$X_3$ is $CH_2$, $CF_2$; S, SO, $SO_2$, O, NH, or $NR^2$, wherein $R^2$ is alkyl; and $X_2$ is halogen, alkyl, halogenated alkyl, alkoxy, halogenated alkoxy, hydroxyalkyl, pyrollyl, optionally substituted aryloxy, alkylamino, dialylamino, carbamyl, amido, alkylamido dialkylamido, acylamino, alkylsulfonylamido, trihalomethoxy, trihalocarbon, thioalkyl, $SO_2$— alkyl, COO-alkyl, $NH_2$, OH, or CN or part of a ring formed by R; and $X_1$ represents one more substituents on the aryl group, with the proviso that $X_1$ represents at least one substituent in the 5'-position said substituent in the 5'-position being selected from the same choices as $X_2$; $C_1$ to $C_6$ alkyl or alkoxy; or wherein $X_1$ has the formula —O—$(CH_2)_n$—O—, wherein n is 1 or 2, and one of the oxygens is bonded at the 5'-position of the aryl ring and the other is bonded to the 4' position.

The ride-side aryl group may be phenyl, or may include one or more heteroatoms. For example, the right-side aryl group may be a nitrogen-containing aromatic heterocycle such as pyrimidine.

In specific embodiments of the composition of the invention, the right-side aryl group is substituted at the 2' and 5' position only. In other embodiment, the right side aryl group is substituted at the 2', 4', and 5' positions. In yet other embodiments, the right side aryl group is substituted at the 4' and 5' positions only. As will be appreciated by persons skilled in the art, the numbering is based on the structure as drawn, and variations in the structure such as the insertion of a heteroatom may alter the numbering for purposes of formal nomenclature.

In other specific embodiments of the composition of the invention, the right side aryl group has a substituent at the 2'-position and $X_1$ has the formula —X—Y—Z— with X and Z connected at the 4' and 5' positions to the right side aryl, wherein X, Y and Z are independently C, N, S or O, connected by single or double bonds and with appropriate hydrogen, alkyl or other substitution to satisfy valence. In some embodiments, at least one of X, Y and Z is a carbon atom. Y in —X—Y—Z may also be —$(CH_2)_2$ such that the X—Y—Z group forms a six-membered ring. In one specific embodiment, $X_1$ is —O—$(CH_2)_n$—O—, wherein n is 1 or 2 from 0 to 2, and one of the oxygen atoms is bonded at the 5'-position of the aryl ring and the other at the 4' position. Additional examples of compounds of this type are shown in the FIG. 4.

In specific embodiments of the invention, R is 3-isopropylaminopropyl, 3-(isopropyl(methyl)amino)propyl, 3-(isopropyl(ethyl)amino)propyl, 3-((2-hydroxyethyl)(isopropyl) amino)propyl, 3-(methyl(prop-2-ynyl)amino)propyl, 3-(allyl(methyl)amino)propyl, 3-(ethyl(methyl)amino)propyl, 3-(cyclopropyl(propyl)amino)propyl, 3-(cyclohexyl(2-hydroxyethyl)amino)propyl, 3-(2-methylaziridin-1-yl)propyl, 3-(piperidin-1-yl)propyl, 3-(4-(2-hydroxyethyl)piperazin-1-yl)propyl, 3-morpholinopropyl, 3-(trimethylammonio)propyl, 2-(isopropylamino)ethyl, 2-(isobutylamino)ethyl, 2-(neopentylamino)ethyl, 2-(cyclopropylmethylamino)ethyl, 2-(ethyl(methyl)amino)ethyl, 2-(isobutyl(methyl)amino)ethyl, or 2-(methyl(prop-2-ynyl) amino)ethyl.

In accordance with specific embodiments of the invention, the purine scaffold composition has a formula as shown in FIG. 5.

The composition of the invention may also be a homodimer or heterodimer of these compounds in which a linker connects the right side aryl group of one moiety to the right side aryl group of another, or in which a linker connects the R group of one moiety to the R group of another provided that the compound retains the ability to inhibit hsp90 and also to cross the blood brain barrier.

Where the active compound in vivo is the dimeric faun, the compound retains the ability to inhibit hsp90 and also to cross the blood brain barrier. In this case, the linker may be any generally linear group of atoms that provides the two parts of the dimer with sufficient rotation freedom to allow both to interact independently with an N-terminal pocket of HSP90. Non-limiting examples of suitable linkers include $C_4$ to $C_{10}$ alkyl, alkenyl or alkynyl groups, and secondary amines having a total length of 4 to 10 atoms.

Compounds of this type may also be provided with a degradable or cleavable linker, such that monomeric agents are provided in vivo. In this embodiment, the dimeric form need not retain activity or the ability to cross the blood brain barrier, and the nature of the linker therefore is not relevant to activity, only to the ability to form active monomeric species. In general, moderately lipophilic drugs such as PUs cross the BBB by passive diffusion. A good structural understanding for the BBB permeability is still lacking, but several parameters are believed to facilitate such behavior. Lipophilicity was the first of the descriptors to be identified as important for CNS penetration. For several classes of CNS active substances, Hansch and Leo (89) found that blood-brain barrier penetration is optimal when the LogP values are in the range of 1.5-2.7, with the mean value of 2.1. The mean value for ClogP for the marketed CNS drugs is 2.5. PU-DZ8 has a calculated logP value of 1.73 (using Molinspiration) and an experimentally determined value of 1.53 (using RP-HPLC). CNS drugs have significantly reduced molecular weights (MW) compared with other therapeutics. The rules for molecular weight in CNS drugs have been reviewed, where small molecules may undergo significant passive lipid-mediated transport through the blood brain barrier, when the molecular mass is kept in or below a 400- to 600-Da range (90). PU-DZ8 has a MW of 512. All the QSAR equations emphasize the importance of hydrogen bonding —CNS penetration requires 5 or less hydrogen bond acceptors (91). PU-DZ8 has 4. PSA has been shown to be a very good descriptor characterizing drug absorption, including intestinal absorption, bioavailability, Caco-2 permeability and BBB penetration. PSA has been used as a predictor for BBB penetration by many investigators (92). In general, drugs aimed at the CNS tend to have lower polar surface areas than other classes (93,94). PSA for CNS drugs is significantly less than for other therapeutics with PSA for CNS penetration estimated at 60-70 $Å^2$ through 90 $Å^2$ (95,96). The upper limit for PSA for a molecule to penetrate the brain is around 90 $Å^2$. DZ8 has a PSA of 104 $Å^2$. Changing the nature of the chain attached to the 9N position from a secondary to a tertiary amine drops the PSA to 90 $Å^2$. Number of rotatable bonds has been shown to be a very good descriptor of oral bioavailability of drugs (97-99). It is suggested that compounds which meet only the two criteria of (1) 10 or fewer rotatable bonds and (2) polar surface area equal to or less than 140 $Å^2$ (or 12 or fewer H-bond donors and acceptors) will have a high probability of good oral bioavailability in the rat (99). Many CNS drugs are basic and exist in equilibrium between their charged and neutral states under physiological conditions or are amphiphilic if they also possess an acidic group. Possession of a positive charge at pH 7-8 tends to favor brain permeation (100). Additionally, compounds possessing a tertiary nitrogen (a feature of many CNS drugs) show a higher degree of brain permeation. All these characteristics are modeled into purine scaffold compounds as described herein.

Another characteristic which is indicative of the ability to cross the blood brain barrier is protein binding. Drug-protein interaction is a reversible process and a successful CNS drug should not be an efficient P-glycoprotein substrate (in vivo) (102). It is not sufficient for a potential neurotherapeutic agent to move across the BBB—it also has to stay in the brain long enough to exert its desired action. This means that it also has to avoid being a substrate for a variety of transport proteins that work to extrude compounds from the brain. The Hsp90 inhibitor 17AAG is a P-gp substrate, however the purine scaffold therapeutic PU-DZ8 is not a substrate of P-pg and thus is not readily extruded from the brain by this mechanism.

Figure 6:
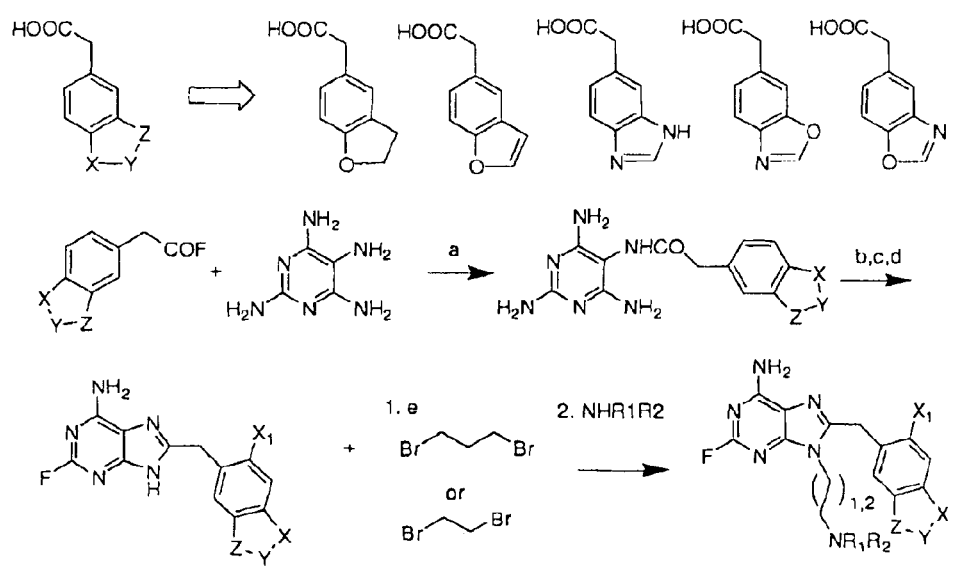
FIG. 6 shows a synthetic scheme for making compounds useful in the invention.
Figure 7:
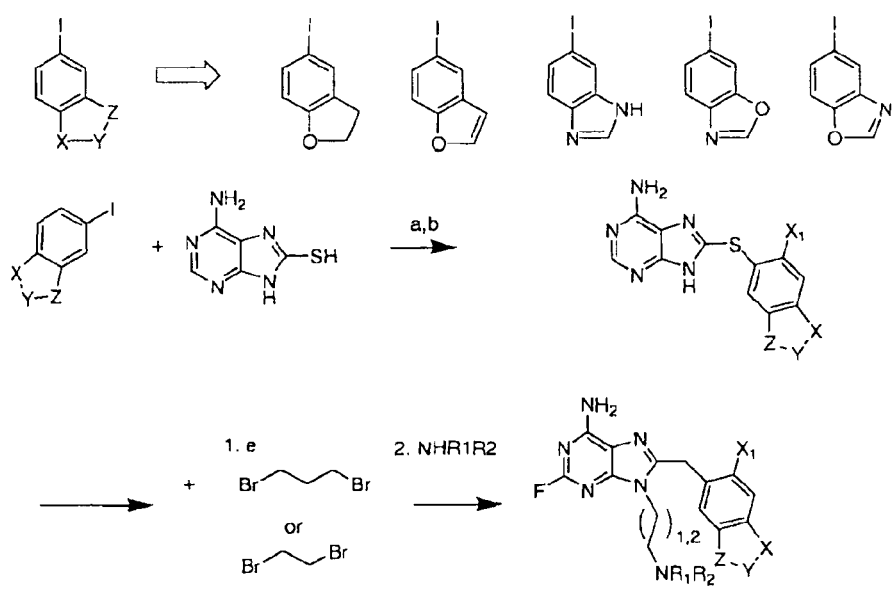
FIG. 7 shows a synthetic scheme for making compounds useful in the invention.

Synthetic methods for making compounds useful in the method of the invention are described in PCT Publication No. WO02/36075, PCT Application No. PCT/US06/03676 and US Patent Publications 2005-0113339, 2005-0004026, 2005-0049263, 2005-0256183, 2005-0119292, 2005-0113340 and 2005-0107343. FIGS. 6 and 7 shows synthetic schemes for making compounds with the structures as shown in FIG. 4. In the case of a carbon linker, phenylacetic acids are first generated by replacing the methylenedioxy bridge with the metabolically stable isosters depicted in FIG. 6. Synthesis commences by coupling 2,4,5,6-tetraminopyrimidine with the acid fluoride of the corresponding carboxylic acid. The acid fluoride is generated by treating the phenylacetic acid with cyanuric fluoride and pyridine in $CH_2Cl_2$. Following a quick water wash, the resulted acid fluoride is used in the next step without further purification. The amide resulted from the pyrimidine-acid fluoride coupling is cyclized to by heating in alcoholic NaOMe. Transformation of the C2-amino group to fluorine ($NH_2$ to F) is conducted by a modified Schiemann diazotization-fluorodediazoniation of the amino derivative in HF/pyridine in the presence of $NaNO_2$. We and others have previously determined that fluorine in this position in general augmented the potency of the resulting purines, likely by increasing the hydrogen donor ability of C6 NH2. Further selective halogenation using either NIS or NBS leads to the corresponding iodo- or bromo-derivatives. These are alkylated first with 1,3-dibromopropane or 1,2-dibromobutane in the presence of $Cs_2CO_3$. Formation of dimer is not detected in this reaction. The resulted bromine is further alkylated in the presence of excess $R_1R_2NH$ to give the final product.

For derivatives containing a sulfur linker, synthesis is carried out using a method previously described by He et al (1) and employs the copper catalyzed coupling of 8-mercaptoadenine with the aryliodide (FIG. 7). The reaction occurs in anhydrous DMF at 110° C. under nitrogen. The 8-arylsulfanyl adenine is further iodinated selectively at position 2 of the aryl moiety using NIS as a source of electrophylic iodine and TFA as a catalyst. This is further alkylated at 9N in the presence of excess $R_1R_2NH$ to give the final product.

Application of the Invention to Tauopathies

Alzheimer's disease (AD) is the most common neurodegenerative disorder characterized by the progressive deterioration of cognition and memory in association with the presence of senile plaques, neurofibrillary tangles, and massive loss of neurons, primarily in the cerebral cortex and hippocampus. Senile plaques are extracellular deposits composed of β-amyloid (Aβ) fibrils, surrounded by dystrophic neurites, reactive microglia and astrocytes. Filamentous Tau inclusions are increasingly recognized as the hallmark of tauopathies, a growing family of neurodegenerative diseases including AD, Down's syndrome (DS), several variants of prion diseases, progressive supranuclear palsy (PSP), amyotrophic lateral sclerosis/parkinsonism-dementia complex of Guam (ALS/PDC), sporadic frontotemporal dementia with parkinsonism (FTDP), Pick's disease and familial FTDP-17 syndromes. Tau is a critical component of the neuronal cytoskeleton. Some of the morphological changes associated with neuronal apoptosis involve a significant modification of the cytoskeletal network, likely to contribute to the subsequent degeneration of neurons, indicating disruption of cytoskeletal network can cause neurodegeneration. In axons, tau protein is one of the predominant microtubule associated proteins (30). It stabilizes microtubules and promotes neurite outgrowth. This apparently beneficial role of tau contrasts with its anomalous behavior in several neurodegenerative diseases, most prominently AD, where it occurs in a highly phosphorylated form, detaches from microtubules, and aggregates. Pathogenic tau mutations or abnormal tau phosphorylation (which occurs in AD and frontotemporal dementias) result in a more rapid development of NFTs and neurologic disease, a feature consistent with the view that these diseases result from tau aggregation (31).

Several mutations in human tau isoforms on chromosome 17 result in a cluster of neurodegenerative diseases, termed "frontotemporal dementia and parkinsonism linked to chromosome 17 (FTDP-17)" and are characterized by the accumulation of neurofibrillary tangles similar to those in AD, in affected brain regions. Biochemical studies of these tau mutants reveal that they are less stable than normal tau and tend to form fibrillar aggregates (32), consistent with the view that tauopathies are diseases related to protein folding and stability. The tau proteins in AD are not mutated, yet nevertheless comprise NFTs. In AD, tau becomes hyperphosphorylated, and it has been hypothesized that this impairs the microtubule stabilizing role of tau Hyperphosphorylated tau is believed to misfold, undergo net dissociation from microtubules, form abnormal filamentous aggregates (paired helical filaments, PHFs) and polymerize into NFTs (33). The central role of protein misfolding in this process is illustrated by observations that the different tau mutations linked to FDTP-17 differ in their levels of phosphorylation and in their effects on microtubules (34). We have shown an inverse relationship between aggregated tau and the levels of heat shock protein (Hsp)70/90 in tau transgenic mice and Alzheimer's disease brains. In various cellular models, increased levels of Hsp70 and Hsp90 promoted tau solubility and tau binding to microtubules, reduced insoluble tau and caused reduced tau phosphorylation. Conversely, lowered levels of Hsp70 and Hsp90 resulted in the opposite effects. We have also demonstrated a direct association of the chaperones with tau proteins. Our results suggested that up-regulation of molecular chaperones may suppress formation of neurofibrillary tangles by partitioning tau into a productive folding pathway and thereby preventing tau aggregation (12).

Hsp90 inhibitors were found to beneficially increase levels of Hsp70 chaperone in other neurodegenerative systems. Induction of chaperones, especially Hsp70 and Hsp40, was found to delay the onset or to diminish the symptoms in folding diseases (3). GM was found to activate a heat shock response and inhibit huntingtin aggregation in a cell culture model of Huntington's disease (16). GM was reported to restore function to a defective heat shock response in scrapie-infected cells (17, 18). Auluck et al (19) reported that treatment of a fly model of Parkinson's disease with GM fully protected against α-synuclein toxicity. These effects were seen without altering the microscopic appearance of neuronal inclusions, suggesting that chaperones "detoxify" the proteins aggregates in a more subtle way than just preventing the formation of protein aggregates. Auluck also suggested that only a modest change or redistribution of chaperones might be sufficient for neuroprotection (19).

These effects of the Hsp90 inhibitors occur by their modulation of the HSF1-hsp90 complexes. In normal cells, the presence of misfolded or aggregated proteins triggers a complex biological response, referred to as the heat shock response (6) This involves the expression of heat shock proteins (HSPs, molecular chaperones) and of proteins involved in the ubiquitin-proteasome pathway. The evolution of such complex machinery testifies to the fact that is necessary for cells to isolate and rapidly clear unfolded proteins as soon as they appear. In unstressed cells, HSF1 forms a dynamic complex with Hsp90 (7). When protein unfolding increases, these non-native proteins compete with HSF1 for Hsp90 binding resulting in an increase in unbound HSF1 and induction of HSPs. When stress-induced synthesis of chaperones is impaired folding diseases are possible (8). As suggested by its regulation of HSF1 activity, interference with Hsp90 activity by Hsp90 inhibitors triggers a heat shock response. The activity of neuronal disease-activated kinases is regulated by Hsp90.

We have also shown that tau phosphorylation levels at pathological sites was reduced after treatment with the Hsp90 inhibitor geldanamycin (GM) in AD cellular models. Cdk5, Gsk3 and MAPK are three major kinases that can phosphorylate tau at the pathological sites. Because phosphorylation releases tau from microtubules and because tau in the PHF is highly phosphorylated, kinases have been viewed suspiciously for a possible role in pathogenesis. There is increasing evidence that CDK5 and GSK3â may be involved in the pathogenesis of several neurodegenerative disorders. In neurons that no longer divide, deregulation of Cdks, especially Cdk5, occurs in many neurological disorders, including Alzheimer's disease (AD) and Parkinson's disease (PD). Fath et al. has shown that replacement of certain amino acids at known sites of phosphorylation with a charged amino acid created 'pseudohyper-phosphorylated' tau that can mimic structural and functional aspects of hyperphosphorylated tau (35). In vivo evidence for an interaction with tau exists for Cdk5 and Gsk3. Over-expression of human p25 (an activator of Cdk5) in mice induced tau hyperphosphorylation and cytoskeletal disruptions reminiscent of AD, but no filamentous deposits (36). Noble et al. crossed transgenic mice over-expressing the Cdk5 activator p25, with transgenic mice over-expressing mutant (P301L) human tau. Tau was hyperphosphorylated at several sites in the double transgenics, and a highly significant accumulation of aggregated tau occurred in the brainstem and cortex. Increased numbers of silver-stained neurofibrillary tangles (NFTs) accompanied these changes as well as an association of active GSK with insoluble tau (37). Over-expression of GSK-3 under the control of a tetracycline sensitive transactivator also induced tau hyperphosphorylation, somatodendritic mislocalization of tau, and neuronal apoptosis (38). Recent studies have shown that the β-amyloid peptide (Aβ) induces a deregulation of Cdk5 in cultured brain cells, and raises the question on the possible roles of this tauphosphorylating protein kinase in the sequence of molecular events leading to neuronal death triggered by Aβ. In this context, there is evidence that Cdk5 is involved in tau hyperphosphorylation promoted by Aβ in its oligomeric form (42). Cdk5 inhibitors protect hippocampal neurons against both tau anomalous phosphorylations and neuronal death. The links between the studies on the Cdk5/p35 system in normal neurogenesis and its claimed participation in neurodegeneration, provide the framework to understand the regulatory relevance of this kinase system, and changes in its regulation that may be implicated in disturbances such as those occurring in Alzheimer disease (70). Overall these studies implicate tau hyper-phosphorylation in tau-related neurodegeneration and allude to Cdk5, Gsk3 and MAPK as major players in the process.

As demonstrated in the examples set forth below, small molecule purine scaffold compounds are able to inactive the kinases involved in tau phosphorylation and when the appropriate substitution patterns are selected are able to cross the blood brain barrier. Further, addition of PU24FC1 Hsp90 inhibitor to a panel of transformed cells led to a dose-dependent induction of Hsp70 and Hsp40. This phenomenon occurred in all the tested cell lines irrespective of their tissue of provenance and was duplicated in rat cortical primary neurons. Doses of PU24FC1 and PU29FC1 (another early PU-class compound) that induce a stress response were not toxic against normal cells, as demonstrated in a panel of normal epithelial and fibroblast cells.

Application of the Invention to Other Neurodegenerative Diseases

Amyotrophic lateral sclerosis is a neurological disorder that selectively affects motor neurons of brain and spinal cord. Amyotrophic lateral sclerosis (ALS) is characterized by a progressive degeneration of motor neurons that results in severe weakness and skeletal muscle atrophy. The disease is progressive and patients usually succumb to bulbar paralysis, cachexia or respiratory failure within 2-5 years of onset (44). A distinguishing feature of ALS is the accumulation of neurofilaments in the perikarya and axons of the spinal motor neurons (for review see Julien 2001, 45). NF—H and NF-M are substrates of CDK5, and the motor neuron inclusion bodies that occur in ALS cases contain hyperphosphorylated NF—H (for review see Julien 1999, 47). Emerging evidence indicates an involvement of the serine/threonine cyclin-dependent kinase 5 (Cdk5) in the pathogenesis. Deregulation of Cdk5 by its truncated coactivators, p25 and p29, contributes to neurodegeneration by altering the phosphorylation state of cytosolic and cytoskeletal proteins and, possibly, through the induction of cell cycle regulators.

Parkinson's disease is characterized by bradykinesia in most patients and many patients may develop a resting tremor (for review see Fahn 2003, 48). Classic pathological findings include loss of neuromelanincontaining neurons within the substantia nigra and the presence Lewy bodies (48). The Lewy body is an eosinophilic cytoplasmic neuronal inclusion (for review see Fahn 2003, 48), and CDK5 immunoreactivity occurs in Lewy bodies in the midbrain of Parkinson's disease patients (22). In rats, induction of apoptosis in neurons of the substantia nigra resulted in increased CDK5 levels and activity at the later stages of apoptosis (49). Further, CDK5 and p35 immunoreactivity was observed in the perikaryon and nuclei of apoptotic neurons, whereas immunoreactivity in healthy neurons was confined to the axons (49).

Other kinases that are also deregulated in PD, and for which pathogenic mutations have been identified in sporadic PD patients are strong candidates as HSP90 clients. These include leucine-rich repeat kinase-2 (LRRK2) gene were pathogenic mutations cause autosomal-dominant and certain cases of sporadic Parkinson disease. The G2019S substitution in LRRK2 is the most common genetic determinant of Parkinson disease identified so far, and maps to a specific region of the kinase domain called the activation segment. Here we show that autophosphorylation of LRRK2 is an intermolecular reaction and targets two residues within the activation segment. The prominent pathogenic G2019S mutation in LRRK2 results in altered autophosphorylation, and increased autophosphorylation and substrate phosphorylation, through a process that seems to involve reorganization of the activation segment. Another mutant kinase in the PTEN induced putative kinase 1 (PINK1) gene. These mutations were originally discovered in three pedigrees with recessively inherited PD. Two homozygous PINK1 mutations were initially identified: a truncating nonsense mutation (W437X) and a G309D missense mutation. Subsequently, multiple additional types of PD-linked mutations or truncations in PINK1 have been reported, making PINK1 the second most common causative gene of recessive PD. Interestingly, despite autosomal recessive transmission of PINK1-linked early-onset PD, a number of heterozygous mutations affecting only one PINK1 allele have been associated with late-onset PD. The pathogenic mechanisms by which PINK1 mutations lead to neurodegeneration are unknown.

PINK1 encodes a 581-amino-acid protein with a predicted N-terminal mitochondrial targeting sequence and a conserved serine/threonine kinase domain. PINK1 protein has been shown to localize in the mitochondria and exhibit autophosphorylation activity in vitro. The in vivo substrate(s) and biochemical function of PINK1 remain unknown. In cultured mammalian cells, overexpression of wild-type PINK1 protects cells against apoptotic stimuli, whereas small interfering RNA (siRNA)-mediated depletion of PINK1 increases the susceptibility to apoptotic cell death. In Drosophila, loss of PINK1 leads to mitochondrial defects and degeneration of muscle and dopaminergic neurons. Despite ample evidence indicating an essential role of PINK1 in cytoprotection, the mechanism by which PINK1 protects against apoptosis is not understood.

Our results showed that at least Cdk5 and P35 are client proteins of Hsp90. Inhibition of Hsp90 could decrease Cdk5/P35 protein level in vitro and P35 level in vivo. Since accumulated evidence implicate that Cdk5/P35 is related to those neurodegenerative diseases, Hsp90 inhibitor can also be used in the treatment of those diseases.

The invention will now be further described with reference to the following, non-limiting examples.

Example 1

Juvenile mice: Four- to six-week old nu/nu athymic female mice were obtained from the National Cancer Institute-Frederick Cancer Center and maintained in ventilated caging. Experiments were carried out under an Institutional Animal Care and Use Committee-approved protocol, and institutional guidelines for the proper and humane use of animals in research were followed. Before administration, a solution of PU24FC1 was prepared at desired concentration in 50 µL vehicle (PBS:DMSO:EtOH at 1:1:1 ratio). In experiments designed to define the short-term effects of PU24FC1 on tau phosphorylation, mice (2 per time point) were treated with 200 mg/kg PU24FC1 or with vehicle alone. At the time of sacrifice, brains were collected and immediately flash frozen. For protein analysis brains were homogenized in SDS lysis buffer (50 mM Tris pH 7.4, 2% SDS). For long-term administration studies, mice (n=5) were treated every other day for 30 days with the indicated doses of PU24FC1. Weight and behavior changes were monitored for all animals. Mice were sacrificed by $CO_2$ euthanasia at 8 h post-last PU24FC1 injection. Brains were collected and processed as mentioned above. Proteins were further analyzed by Western blot.

Figure 1B:
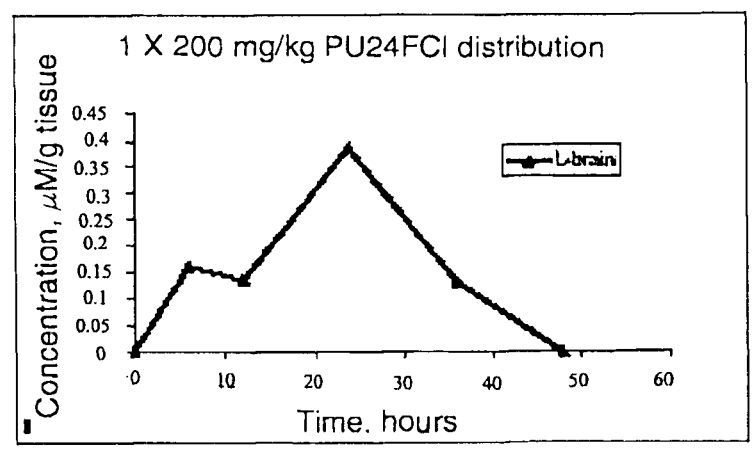
FIG. 1B shows concentration of PU24FC1 in mouse brain following short term administration.

Phosphorylation of tau in juvenile and embryonic brains is enhanced (50) and similar to AD afflicted brain (51; 52). Further, nude athymic mice 4-6 weeks of age may express tau phosphorylated at relevant disease epitopes In a first in vivo experiment, the short term modulation of Hsp90 in the brains of these animals was evaluated. One dose of PU24FC1 (200 mg/kg) was administered intraperitoneally to these mice and animals were sacrificed at 0, 6, 12, 24, 36 and 48 hours. Whole brains were homogenized in lysing buffer and tau phosphorylation at S202/T205 was evaluated by Western blot. A burst in tau phosphorylation at this epitope was observed 12 h post-administration, with a decline to basal levels shortly after (FIG. 1A). Drug levels in the brain tissue were analyzed by LC-MS and showed the presence in brain tissue at therapeutically relevant levels with a spike at around 24 hours (FIG. 1B). In these same mice, PU24FC1 was quickly cleared from the liver, serum and uterus.

Figure 2:
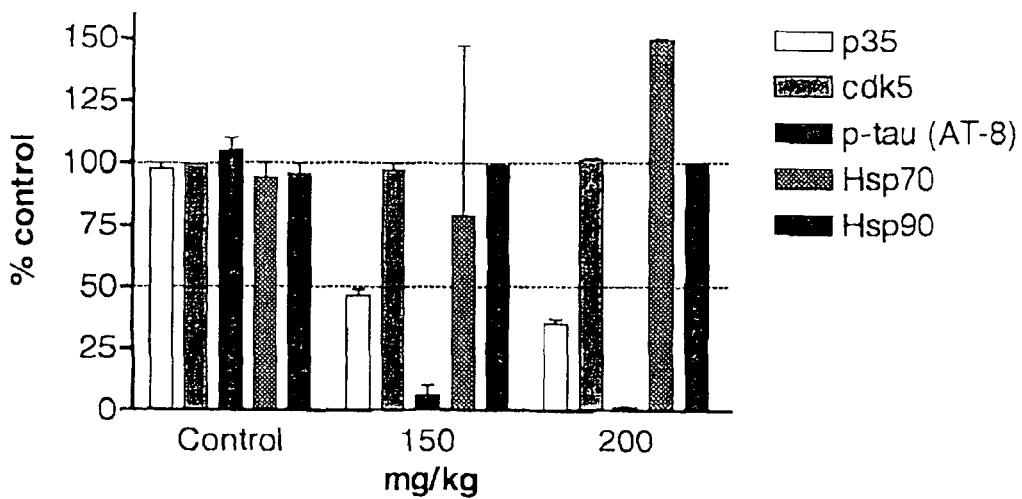
FIG. 2 shows the effects of long-term Hsp90 inhibition with PU24FC1 on tau phosphorylation and expression of other proteins.

In a second experiment, we analyzed the effects of long-term Hsp90 inhibition on tau phosphorylation Mice were treated on alternate days for 30 days with PU24FC1 without observing remarkable toxicity or weight loss in these animals. As seen in FIG. 2, a significant decrease in tau phosphorylation at S202/T205 was evident in all treated mice. Such difference in effects between short and long term modulation of Hsp90 has been documented for other proteins chaperoned by Hsp90. Treatment of cells with Hsp90 inhibitors caused degradation of Raf-1 over a long time course, while inducing a transient burst of Raf-1 activity when administered for a short time (53). Similar evidence has been demonstrated for the activity of the RNAdependent kinase PKR, which becomes active upon short treatment with GM (54). These observations suggest that Hsp90 may act to restrain the basal signaling of these kinases. Additional examples are found in the regulation of steroid hormone receptors. Hsp90 masks dimerization and inhibits DNA binding of steroid hormone receptors until chaperone interactions are interrupted, typically as a consequence of hormone binding. Thus, steroid hormone receptors stripped from chaperones are competent for dimerization and DNA binding in the absence of hormone (55). While this function of Hsp90 may not hold true for all its client proteins, in the case of p35/cdk5, Hsp90 may undertake a similar role restraining the intrinsic activity of the complex, while retaining it in a primed conformation, ready for interaction with tau.

Reduction in tau phosphorylation in the long-term treatment experiment was associated with a 60 to 70% decrease in p35 expression (FIG. 2). In addition, an increase in the expression of the inducible Hsp70 was observed in these mice (FIG. 2). Expression of cdk5 in the whole brain was not affected. The cdk5 protein is widely distributed in mammalian tissues and in cultured cell lines and is complexed with an array of other proteins, with each association serving a diverse cellular role. The cdk5/p35 associated kinase activity has been demonstrated only in the cerebral cortex (56, 57). When immunoprecipitated cdk5 activity was examined in AD brains it was found to be elevated in the prefrontal cortex (58). The limited localization of p35/cdk5 in the cortex may explain why total cdk5 expression in the whole brain was unchanged upon Hsp90 inhibition. Very likely, the high background caused by cdk5 localized to other compartments made impossible monitoring a small change in cdk5 steady-states by Western blot. These results may also suggest that management of cdk5 by Hsp90 in the brain is likely limited to regulating the activity of the p35/cdk5 complex.

Example 2

Transgenic mice: Transgenic mice, JNPL3 line (59) over-expressing mutant human tau (P301L, 4R0N) were used in this study, Mice were heterozygous and on a mixed hybrid genetic background composed of C57BL/DBA2/SW, as published in ref. 59. These mice develop NFTs in the basal telencephalon, diencephalon, brainstem, and spinal cord, with severe pathology accompanied by degeneration in the spinal cord leading to dystonia, paralysis, and death in mice>12 months in age. Nine month-old male JNPL3 mice (n=2) were treated intraperitoneally with PU-DZ8 or vehicle for 5 days. Mice were sacrificed 12 h after last treatment by cervical dislocation under anesthesia.

Figure 3:
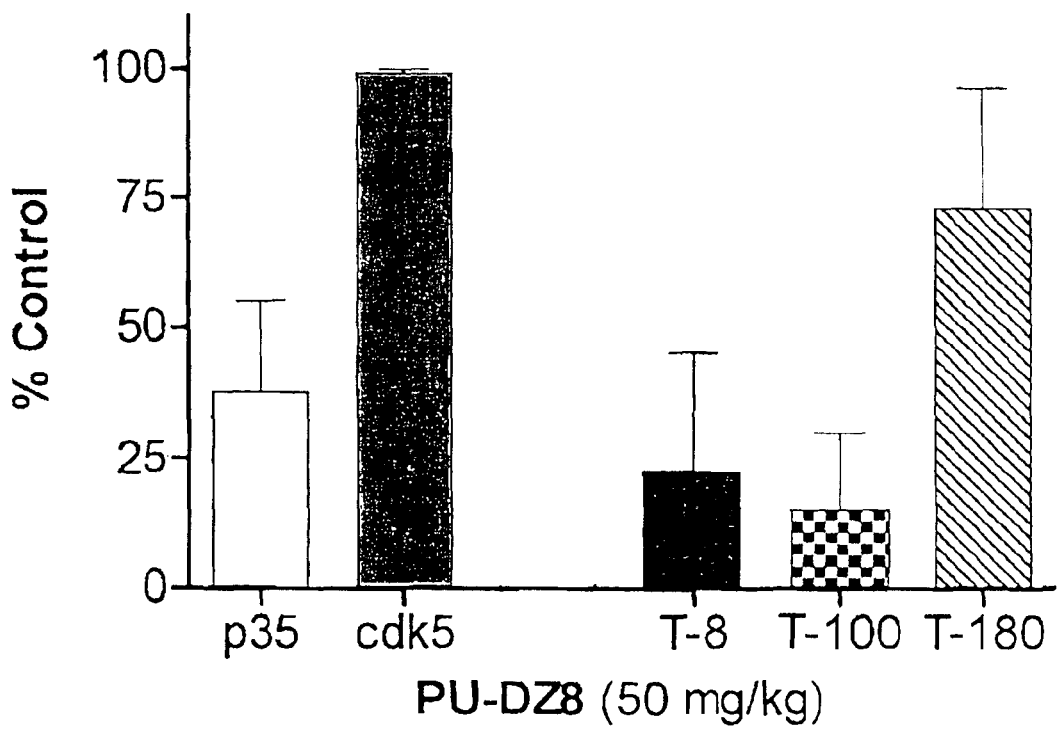
FIG. 3 shows the effects of long-term Hsp90 inhibition with PU-DZ8 on tau phosphorylation.

To further examine the effect of Hsp90 on tau phosphorylation, we used the JNPL3 line of mice expressing mutant (P301L) tau protein (59). Genetic analyses have linked mutations in the tau gene to FTDP-17 (60, 61). Over 20 distinct pathogenic mutations have been identified, with P301L as the most common mutation in tauophaties (33). JNPL3 mice exhibit an age and gene-dose-dependent increase in tau phosphorylation and development of NFTs (59, 62). The tau protein in JNPL3 is predominantly human and is phosphorylated at multiple sites: T181 (AT270), S202/T205 (AT8), T212 (AT100), T231 (AT180), S262, S396/S404, S409 and 5422 (59, 62). In concordance with the experiments in the juvenile nude athymic mice, a five day treatment of nine-month old male JNPL3 mice with PU-DZ8, a water soluble PU24FC1 derivative (2), reduced p35 levels in whole brains and led to a significant amelioration of tau phosphorylation at the putative cdk5 sites, S202/T205 and T212. The degree of p35 expression translated well into alleviation of phosphorylation. A 50% reduction in p35 levels translated in approximately similar effect on S202/T205 (Ab AT-8), while reducing phosphorylation on T212/S214 (Ab AT-100) almost completely. No significant effect on tau phosphorylated at T231 (Ab AT-180), associated with tau in PHF and tangles (63, 64) was seen at a reduction by 50% in p35 expression. However, in mice where effects were more prominent and p35 expression declined to approximately 20% as compared to control, a significant effect on tau phosphorylation at S202/T205 and T212/S214 and a 50% reduction on T231 was observed. We could not detect a significant amount of tau phosphorylation at T181, site found to be hyperphosphorylated in PHF, tangles and neurofilaments (65). Again, whole brain expression of cdk5 was not affected (FIG. 3).

Pharmacologically relevant levels of PU-DZ8 were recorded in these brains.

Example 3

Figure 8A:
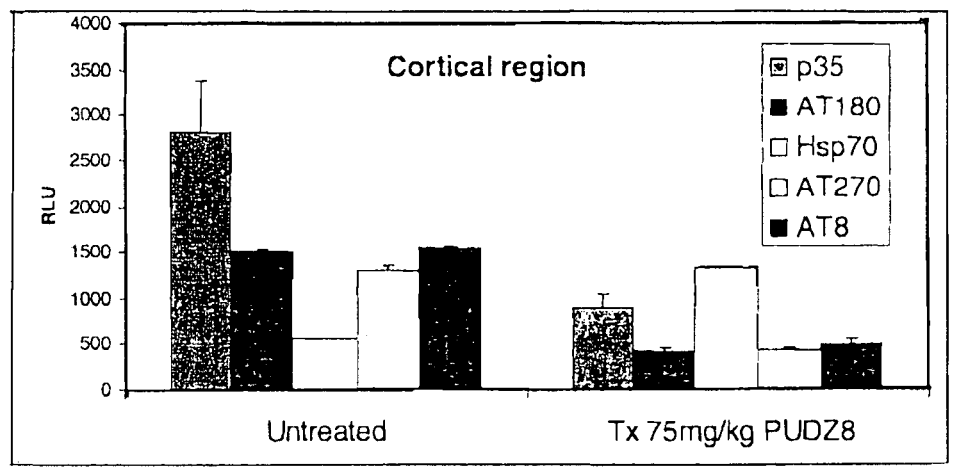
FIGS. 8A and B shows levels of various proteins in the brains of mice treated in accordance with the invention by intraperitoneal administration of a purine scaffold compound.
Figure 8B:
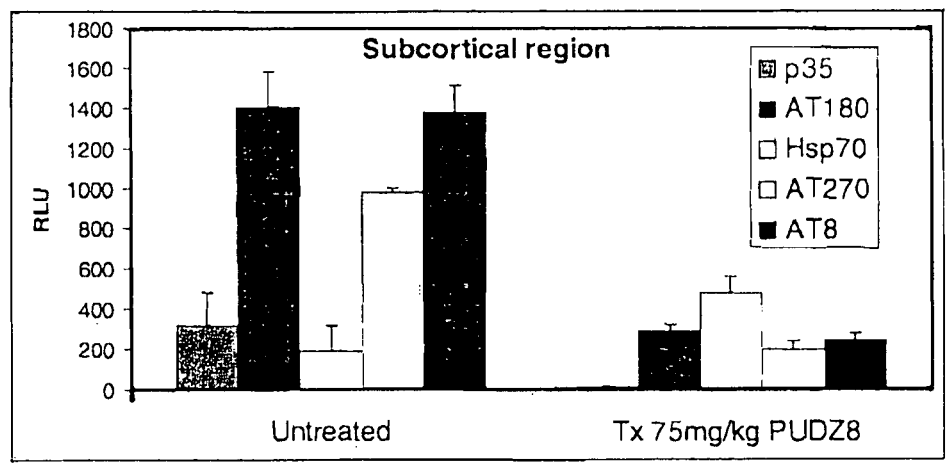

JNPL3 female mice 6.5 months of age were treated for 30 days, 5 day/week, with the Hsp90 inhibitor PU-DZ8 (FIG. 5) or vehicle, or sacrificed for time zero, n=4/group. Brains were divided in subcortical and cortical regions and processed using the Greenberg and Davies extraction protocol. (77) Sarkosyl soluble fractions (S1) were analyzed by WB for p35 and Hsp70, and for tau epitopes found abnormally hyperphosphorylated in AD brains such as: 5202 and T205 recognized by ATB, T181 by AT270, T231 by AT180. These are putative cdk5/p35 sites. Protein bands were normalized to Hsp90 and plotted as relative units. The results are shown in FIGS. 8A and B. Since tauopathy, characterized by pathogenic phosphorylation of tau can be due to aberrant kinase activity, the hsp90 inhibitor is effective because it affects the expression of the p35 protein, an activator of cdk5 known to phosphorylate tau at pathogenic sites, and thus alleviates tau phosphorylation at these sites.

Example 4

Figure 9:
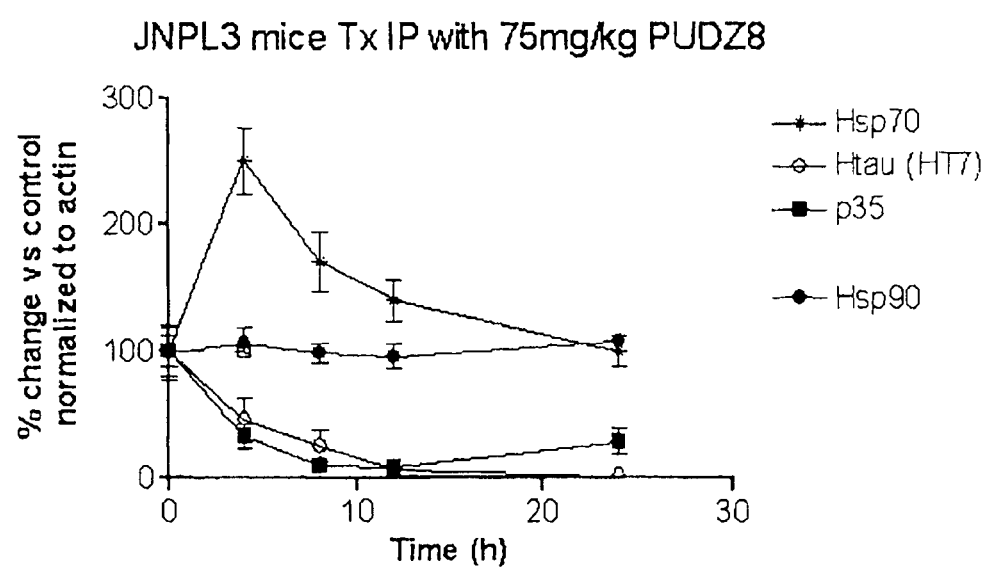
FIG. 9 shows degradation of the mutant protein, mtau (HT7) after one dose administration of PU-DZ8. It also shows the change in chaperone levels (hsp70 increase) and kinase expression (p35 levels).

JNPL3 female mice 6 months of age were treated IP with the Hsp90 inhibitor PU-DZ8 (75 mg/kg) and sacrificed various times as indicated in FIG. 9. Brains were divided in subcortical and cortical regions and processed using the Greenberg and Davies extraction protocol (77). Sarkosyl soluble fractions (S1) extracted from the subcortical region were analyzed by WB for p35, cdk5, mutant tau (HT7), Hsp90 and Hsp70. Protein bands were normalized to actin and plotted as relative change from untreated mice. FIG. 9 shows degradation of the mutant protein, mtau (HT7) after one dose administration of DZ8. It also shows the change in chaperone levels (hsp70 increase) and kinase expression (p35 levels).

Example 5

Figure 10:
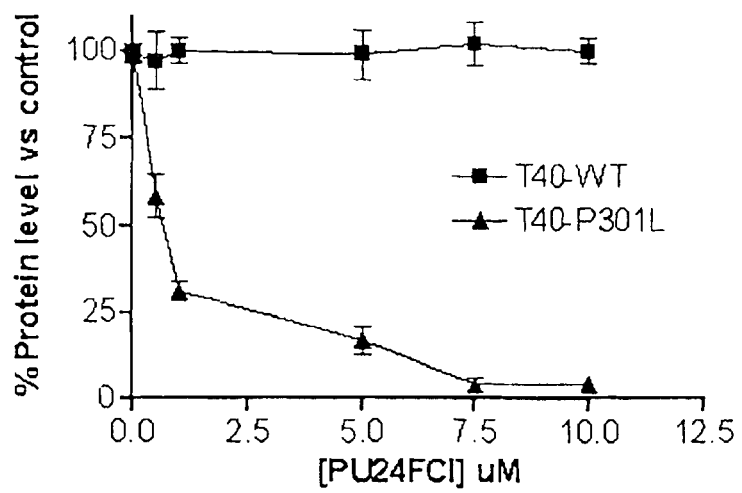
FIG. 10 shows the dependency of mutant tau protein on hsp90 chaperoning.

COS-7 cells were transfected with cDNAs corresponding to WT and mTau and cells were further treated with PU24FC1 for 24 h. Cells were lysed and protein content analyzed by Western blot. The results are shown in FIG. 10. As shown, the mutant Tau (P301L) is very sensitive to the Hsp90 inhibitor PU24FC1, while the WT tau is unaffected by similar doses of drug.

Example 6

Figure 11:
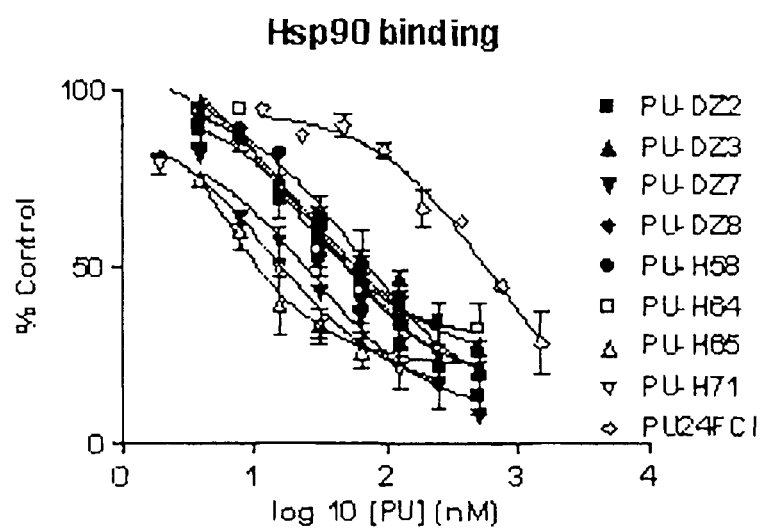
FIGS. 11 A and B show hsp90 binding and hsp70 induction by purine scaffold compounds in neuroblastoma cells.
Figure 11:
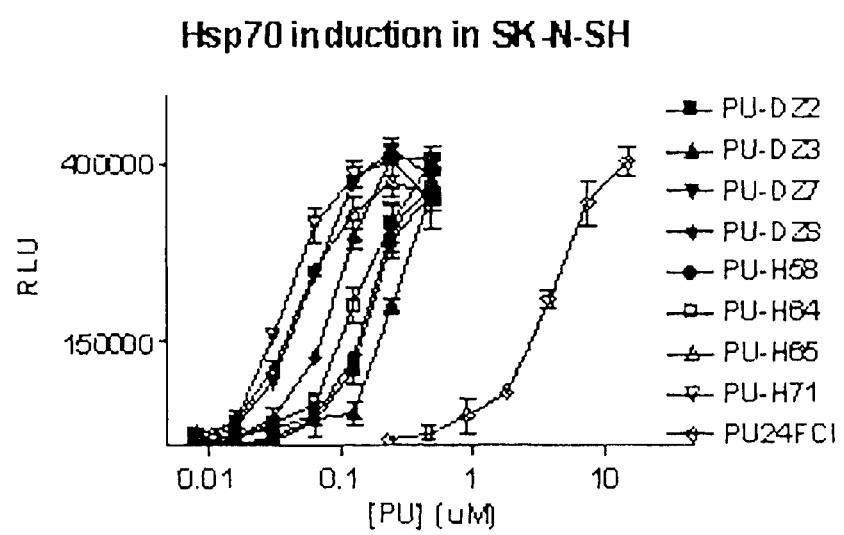

The ability of composition according to the inventions Hsp90 inhibitors to bind Hsp90 was tested using a fluorescence polarization assay developed by Chiosis et al (WO2005012482, 66, 67, 68). SK-N-SH neuroblastoma cells were treated with Hsp90 inhibitors for 24 h and Hsp70 levels were detected by a phenotypic cell-based assay developed by Chiosis et al (WO2005012482,69). The results are summarized in FIGS. 11 A and B. As shown, the inhibitors induce a stress response in the SK-N-SH neuroblastoma cells and Hsp70 induction by Hsp90 inhibitors correlates with their potency in binding to the ATP-regulatory pocket of the Hsp90 chaperone.

Example 7

Embryonic primary rat cortical neurons and COS-7 cells transfected with cDNAs corresponding to either p35 alone (COS-7/p35) or both p35 and Tau (COS-7/p35/Tau) are relevant experimental systems to study aberrant neuronal kinase activity because phosphorylation of Tau at putative cdk5 sites is both enhanced in these cells and in embryonic and juvenile brains (50, 52) and is similar to that in AD-afflicted brains (50). COS-7 cells transfected with cDNAs corresponding to either humanWT Tau (COS-7/Tau) or Tau harboring the P301L mutation characteristic of frontotemporal dementia and parkinsonism linked to chromosome 7 (COS-7/TauP301L) are cellular models that may be used to differentiate the effect of Hsp90 inhibition on a mutant protein compared with its normal counterpart.

To further examine the roles played by Hsp90 in tauopathy, we made use of both PU24FC1 and 17-(allyllamino)-17-demethoxygeldanamycin (17AAG) and investigated their effects on both cdk5/p35 and TauP301L in primary neuronal and COS-7 cell cultures. Primary neuronal cultures were derived from the cerebral cortices of embryonic day 17 rat embryos and maintained as described previously (105). To determine the effects of PU24FC1 on protein steady-states and on Tau phosphorylation, PU24FC1 was added at day 6 of culture, and cells were incubated at 37° C. as indicated. COS-7 cells grown in DMEM with 10% FBS and penicillin/streptomycin (50 units and 50 µg/ml, respectively) were transiently transfected by using FuGENE 6 reagent (Roche Molecular Biochemicals, Indianapolis, Ind.) to over-express p35 and either WT Tau or Tau harboring a P301L mutation. At 12 h after transfection, cells were incubated for 24 h with the indicated concentration of PU24FC1. After incubation, cells were harvested and lysed in 2% SDS, and the resulting samples were analyzed by Western blotting.

Phosphorylation of Tau by cdk5 is initiated through activation by complex formation with one of the neuron-specific proteins p35 or p39. However, only suppression of p35 by antisense oligonucleotide treatment but not of the highly related isoform p39 selectively reduces cdk5 activity. In addition, levels of p35 but not of cdk5 protein are rate-limiting for cdk5 activity. In concordance, we assessed the influence of Hsp90 inhibition on p35 cellular expression. A dose- and time-dependent degradation of p35 by PU24FC1 was detected in primary neurons by immunoblot and by immunofluorescence techniques, as well as in COS-7/p35 and COS-7/p35/Tau cells. Effects were seen at ~1-5 µM PU24FC1 and were maximal at 10 µM Hsp90 inhibitor, in agreement with the affinity of this compound for Hsp90. Exogenously introduced p35 was more sensitive to Hsp90 inhibition than the endogenous protein, suggesting that by analogy to Hsp90 oncoproteins, buffering and stabilization of aberrant proteins in tauopathy may be accomplished by co-opting Hsp90. Reduction of p35 levels by Hsp90 inhibition affected the activity of the cdk5/p35 complex, as measured by using a substrate of cdk5, the histone-H1, and lessened Tau phosphorylation at putative cdk5 shown to be phosphorylated in AD brains without affecting normal Tau protein expression. mTau however, was sensitive to concentrations of PU24FC1 that did not interfere with WT Tau expression. The higher sensitivity to Hsp90 inhibition of mTau compared with WT Tau is in agreement with the observed lability of the mutant oncoprotein clients of Hsp90. Analogous effects on p35 and mTau were observed with 17AAG. The effect of PU24FC1 on neuronal proteins was well-defined and selective, as the expression of several kinases and phosphatases that regulate normal Tau activity (PKA, CK-1, CK-2, PP-1-alpha, PP-1-gamma, and PP2A) was not affected by the Hsp90 inhibitor.

Induction of Hsp70 by Hsp90 inhibitors is documented in several neurodegenerative disease models (12, 16, 19). Expression of Hsp70 is indirectly regulated by Hsp90 (7). Accordingly, treatment of either primary neurons or transfected COS-7 cells with PU24FC1 led to a dose-dependent increase in Hsp70. Induction of Hsp70 occurred at doses of PU24FC1 that also modulated both p35 and mTau, suggesting that degradation of aberrant proteins and induction of a heat-shock response are both direct consequences of Hsp90 inhibition by PU24FC1.

Example 8

To examine whether Hsp90 plays a direct role in maintaining the stability of these p35 and mTau, we tested whether inhibition of Hsp90 function by PU24FC1 affected their half-life. Primary neuronal cultures were treated with inhibitor or vehicle in the presence of cycloheximide. Quantification of protein levels demonstrated that the half-life of endogenous p35 was 120 min in the presence of vehicle and decreased to 60 min when PU24FC1 was added to the system. The exogenous p35 was more labile and had a significantly shorter half-life than the endogenous protein ($t_{1/2}$=60 min in the presence of vehicle and 30 min in the presence of PU24FC1) for both COS-7/p35/Tau cells and primary neurons. Similar results were observed for mTau: whereas 50% of the protein was degraded at 2-4 h in the presence of the Hsp90 inhibitor, the half-life of mTau in vehicle treated cells exceeded 10 h. The inhibitor had no effect on the level of WT Tau. Moreover, mTau and p35 were degraded upon PU24FC1 treatment even when induction of Hsp70 was blocked by cycloheximide. These findings strongly position Hsp90 as a direct and important regulator of both p35 and mutant Tau stability.

Example 9

To examine whether Hsp90 regulates the stability of these proteins through protein complex formation, we made use of several chemical and immunological tools that selectively bind either Hsp90 or its putative client proteins. Association of Hsp90 with p35 as well as with mTau, was observed. No significant association was observed when cells were immunopurified with a control IgG. Cdc37, a cochaperone of Hsp90 found associated with several chaperone-kinase assemblies, was absent in the p35-immunopurified complexes, in concordance with previous observations of Lamphere et al. (106). Pretreatment of cells with PU24FC1 altered the interaction of Hsp90 with p35.

The cellular models presented above demonstrate that an interaction between Hsp90 and aberrant neuronal proteins is possible at a molecular level. However, exogenous introduction of proteins by transfection, may destabilize the cell's protein content and impose a regulation of the alien protein's stability by Hsp90. Therefore, to evaluate the interaction of Hsp90 with TauP301L and p35 in an endogenous environment, we made use of brain homogenates obtained from animal models of tauopathy. The JNPL3 line of mice expressing mutant (P301L) human Tau (hTau) protein exhibit an age, gender and gene dose-dependent increase in Tau phosphorylation and insoluble Tau deposits. To isolate proteins associated with Hsp90 in these brains, we made use of brain homogenates obtained from female JNPL3 mice (n=4) 10 months of age and used either a biotinylated PU derivative immobilized on streptavidin beads or a specific anti-Hsp90 antibody. Hsp90 isolated by PU beads bound mTau specifically. The presence of the C terminus of heat-shock cognate 70-interacting protein, an ubiquitin E3 ligase found to collaborate with molecular chaperones in facilitating protein folding, was also identified in the Hsp90 complex, in agreement with findings of Sahara et al. (62). An Hsp90 antibody specifically identified the chaperone in complex with p35 and its kinase partner cdk5. Collectively, these data position Hsp90 as a regulator of p35 and mTau stability through direct protein complex formation.

Example 10

Binding to JNPL3 brain Hsp90. The assay buffer (HFB) contained 20 mM HEPES (K) pH 7.3, 50 mM KCl, 5 mM $MgCl_2$, 20 mM $Na_2MoO_4$, 0.01% NP40. Before each use, 0.1 mg/mL bovine gamma globulin (BGG) (Panvera Corporation, Madison, Wis.) and 2 mM DTT (Fisher Biotech, Fair Lawn, N.J.) were freshly added. GM-cy3B, a specific Hsp90 ligand, was synthesized as previously reported (10) and was dissolved in DMSO to form 10 μM solutions. Brains were homogenized in HFB with added protease and phosphatase inhibitors. Saturation curves were recorded in which GM-cy3B (3 nM) was treated with increasing amounts of brain homogenates. The Hill and Scatchard plot analyses of the experiment were constructed to show that at the low amounts of brain homogenates required to reach saturation, interaction from other cellular material was precluded. The amount of brain homogenate for which over 90% of GM-cy3B was Hsp90 bound at equilibrium (24 h) was chosen for the competition study. For the competition experiments, each 96-well contained 3 nM GM-cy3B, brain homogenate and tested inhibitor (initial stock in DMSO) in a final volume of 100 μL. The plate was left on a shaker at 4° C. for 24 h and the fluorescence polarization values in mP were recorded. $EC_{50}$ values were determined as the competitor concentrations at which 50% of GM-cy3B was displaced. Fluorescence polarization measurements were performed on an Analyst GT instrument (Molecular Devices, Sunnyvale, Calif.). For GM-cy3B, an excitation filter at 545 nm and an emission filter at 610 to 675 nm were used with a dichroic mirror of 565 nm. Measurements were taken in black 96-well microtiter plates.

Figure 12:
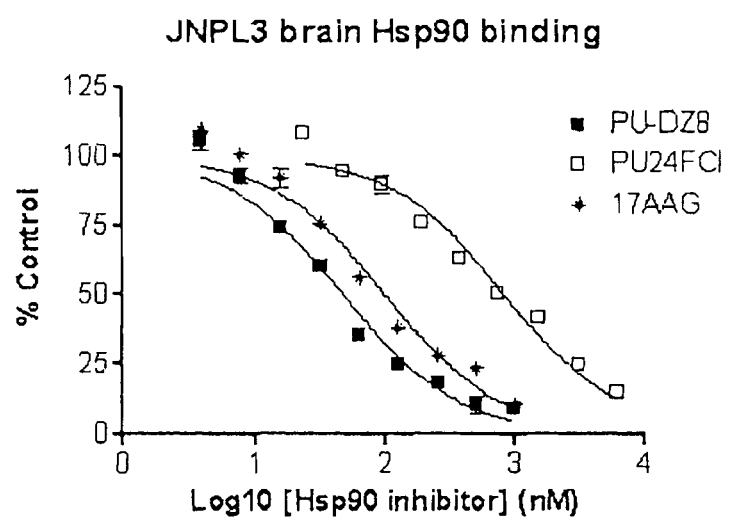
FIG. 12 shows the binding affinity of PU-DZ8, PU24FC1 and 17AAG to hsp90 in JNPL3 brain extracts.

FIG. 12 shows the binding affinity of PU-DZ8, PU24FC1 and 17AAG to hsp90 in JNPL3 brain extracts determined using this procedure. As shown, the $EC_{50}$ for PU-DZ8 is lower than that of the other compounds. (46.71 nM, as opposed to 822.6 nM for PU24FC1 and 98.40 nM for 17AAG).

The same procedure was repeated using the compounds of FIG. 5. The $EC_{50}$ values determined for these compounds are set forth in Table 1. Hsp70 induction in neuroblastoma cells by the various purine scaffold compounds was determined. The potency for hsp70 induction corresponds to the hsp90 binding affinity.

TABLE 1

| Compound | $EC_{50}$ |
|---|---|
| PU-H71 | 0.03084 |
| PU-HT65 | 0.2129 |
| PU-HT64 | 0.1224 |
| PU-DZ8 (multiple measurements) | 0.08533, 0.03598 |
| PU-DZ10 | 0.1928 |
| PU-HT70 | 0.1466 |
| PU-HT78 | 9.561 |

TABLE 1-continued

| Compound | EC$_{50}$ |
|---|---|
| PU-HT133 | 0.8129 |
| PU-BSI12 | 0.03935 |
| PU-BSI6 | 0.06080 |
| PU-BSI11 | 0.20996 |
| PU-BSI7 | 0.04450 |
| PU-BSI14 | 0.04284 |
| PU-BSI15 | 0.02430, 0.1122 |
| PU-BSI4 | 0.03548, 0.1552 |
| PU-BSI10 | 0.1054 |
| PU-BSI3 | 0.1994 |
| PU-BSI16 | 0.2024 |
| PU-DZ12 | 0.2190 |
| PU-DZ13 | 0.01960 |
| PU-DZ14 | 0.02353 |
| PU-DZ16 | 0.03563 |
| PU-DZ15 | 0.1656 |
| PU-DZ17 | 0.09232 |
| PU-DZ18 | 0.1071 |

Example 11

Assessment of PU-DZ8 brain levels. Concentrations of compound were determined and quantitated by a MRM mode using a tandem high-performance liquid chromatography-mass/mass spectrometry (HPLC/MS/MS). A weighed piece of brain was rinsed with saline isotonic solution, dried with gauze and then homogenized in mobile phase (acetonitrile (ACN)/0.1% formic acid=1.2/2.8, v/v). Haloperidol was added as internal standard. PU-DZ8 was extracted in methylene chloride, the organic layer was separated, speedily dried under vacuum and reconstituted in the mobile phase. Compound analysis was performed in the API 4000™ LC/MS/MS (Applied Biosystems) which was coupled with a Shimadzu LC system and a 96-well plate autosampler. A Gemini C18 column (5µ particle size, 50×4.6 mm I.D.) was used for the LC separation. The analyte was eluted under an isocratic condition for 4 min at a flow rate of 0.4 mL/min One dose of PU-DZ8 (75 mg/kg) was administered intraperitoneally (i.p.) to female mice of 2.5-4 months in age (n=32) and animals were sacrificed in the interval of 0 to 36 h. Both aggregate-free Tau (S1) and insoluble Tau (P3) fractions were prepared from the subcortical and cortical regions of these mice. PU-DZ8 levels in the brain reached 0.35 µg/g (~700 nM) at 4 h, and the pharmacologically relevant dose was retained for at least 12 h post-administration (0.2 µg/g, ~390 nM). The results are shown in FIG. 13.

Figure 13:
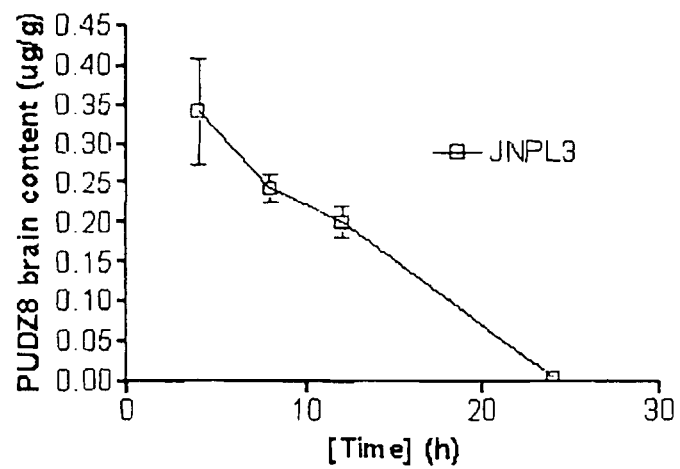
FIG. 13 shows that PU-DZ8 reaches pharmacologically relevant concentrations in JNPL3 transgenic mouse brain following administration of one dose of 75 mg/kg PU-DZ8 administered i.p.

FIG. 13 shows that PU-DZ8 reaches pharmacologically relevant concentrations in JNPL3 transgenic mouse brain following administration of one dose of 75 mg/kg PU-DZ8 administered i.p. This shows that PU-DZ8 arrives in the brain tissue much sooner than PU24FC1 (FIG. 1B).

Example 12

In a cluster of tauopathies termed "frontotemporal dementia and parkinsonism linked to chromosome 17 (FTDP-17)", transformation is caused by several mutations in human Tau isoforms on chromosome 17, that result in and are characterized by the accumulation of aggregated Tau similar to that in AD (10, 11). Over 20 distinct pathogenic mutations have been identified, with P301L as the most common mutation in tauopathies.

To investigate whether release of mTau and p35 from Hsp90 regulation restores normal neuronal activity and results in elimination of toxic Tau aggregates, we made use of the JNPL3 mouse model of tauopathy. Brain tissues of JNPL3 mice contain Tau proteins with different solubilities and these can be separated into buffer-extractable (S1), high-salt extractable (S2) and sarkosyl-insoluble (P3) fractions. The S1 fractions contain a 50-60 kDa human Tau protein, whereas sarkosyl-insoluble Tau proteins of 64 kDa and higher molecular weights are detected in the subcortical brain regions of JNPL3 mice as early as 3 months in hemizygous females. These contain insoluble toxic Tau phosphorylated at multiple sites such as T181, S202/T205, T212 and T231 (37, 38).

Figure 14A:
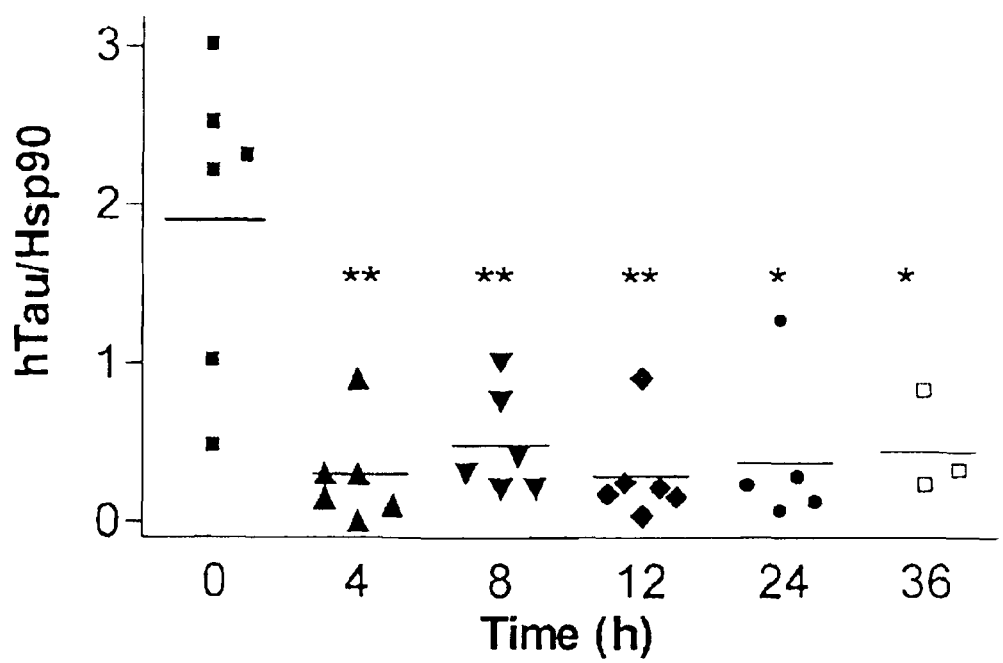
FIG. 14A shows the effects of one dose, short term administration of PU-DZ8 on the levels of soluble mutant tau in the JNPL3 mouse brain The subcortical brain region of 2.5 to 4-month old mice is presented. Human Tau levels were normalized to those of Hsp90.

To investigate whether the human TauP301L present in the JNPL3 line of mice is a sensitive target for Hsp90 inhibition, animals were treated with the brain-barrier permeable Hsp90 inhibitor PU-DZ8. This agent is a higher-potency water soluble derivative of PU24FC1 (EC50JNPL3 brain Hsp90=70 nM). One dose of PU-DZ8 (75 mg/kg) was administered intraperitoneally (i.p.) to female mice of 2.5-4 months in age (n=32) and animals were sacrificed in the interval of 0 to 36 h. Both aggregate-free Tau (S1) and insoluble Tau (P3) fractions were prepared from the subcortical and cortical regions of these mice. Human Tau levels were assessed by immunobloting with a human specific anti-Tau antibody (HT-7). At 4 h post-administration, the Hsp90 inhibitor induced a significant decrease in the soluble precursor pool mTau as present in the subcortical brain regions (P=0.0031 at 4 h), with these effects maintained up to 36 h (P=0.0066 at 8 h, 0.0030 at 12 h, 0.0111 at 24 h and 0.042 at 36 h) (FIG. 14A). We next examined in a 4- to 6-month old mouse group (n=15) whether the stability of mTau as present in tau aggregates (P3 fraction) was additionally regulated by Hsp90. As demonstrated in FIG. 14B, a significant reduction of insoluble (P<0.0001) and hyperphosphorylated (P=0.001) Tau was observed in treated mice (n=8), as compared to those mice receiving no Hsp90 inhibitor (n=7).

No significant changes in cdk5 expression were detected, indicating that management of cdk5 by Hsp90 in the brain may be limited to regulating the activity of the p35/cdk5 complex. The expressions of Akt and Raf-1, nodal proteins in cell survival and growth pathways, respectively, tightly regulated by Hsp90 in malignant cells were not altered by PU-DZ8.

For experiments designed to test the kinetics of mTau and p35 modulation by Hsp90 inhibitors, animals were administered intraperitoneally (i.p.) 75 mg/kg PU-DZ8 in PBS (6% DMSO). Mice were sacrificed by CO2 euthanasia at the indicated times following PU-DZ8 administration. Hemibrains were separated into cortico-limbic (cortex, amygdale and hippocampus) and subcortical (basal ganglia, diencephalon, brain stem and cerebellum) regions, quickly frozen on dry ice and stored at −80° C. and processed. In summary, each brain piece was weighed and homogenized in three volumes of Tris-buffered saline (TBS) containing protease and phosphatase inhibitors (25 mM Tris-HCl, pH 7.4, 150 mM NaCl, 1 mM EDTA, 1 mM EGTA, 5 mM sodium pyrophosphate, 30 mM β-glycerophosphate, 30 mM sodium fluoride, 1 mM phenylmethylsulfonyl fluoride (PMSF)). The homogenates were centrifuged at 27,000 g for 15 min at 4° C. Supernatants were collected as S1 fractions, and the pellets (P1) were re-homogenized in three volumes of salt/sucrose buffer (0.8 M NaCl, 10% sucrose, 10 mM Tris/HCl, pH 7.4, 1 mM EGTA, 1 mM PMSF) and centrifuged as above. The resulting pellets were discarded and the supernatants were incubated with sarkosyl (Sigma, St Louis, Mo., USA; 1% final concentration) for 1 h at 37° C. The sarkosyl mixtures were then centrifuged at 150,000 g for 30 min at 4° C. The supernatants (S2 fraction) were collected, and the pellets (P3) were resuspended in 50 μL 2% SDS in TBS and stored at −80° C. for western blotting. Proteins were analyzed by Western blot.

Figure 14B:
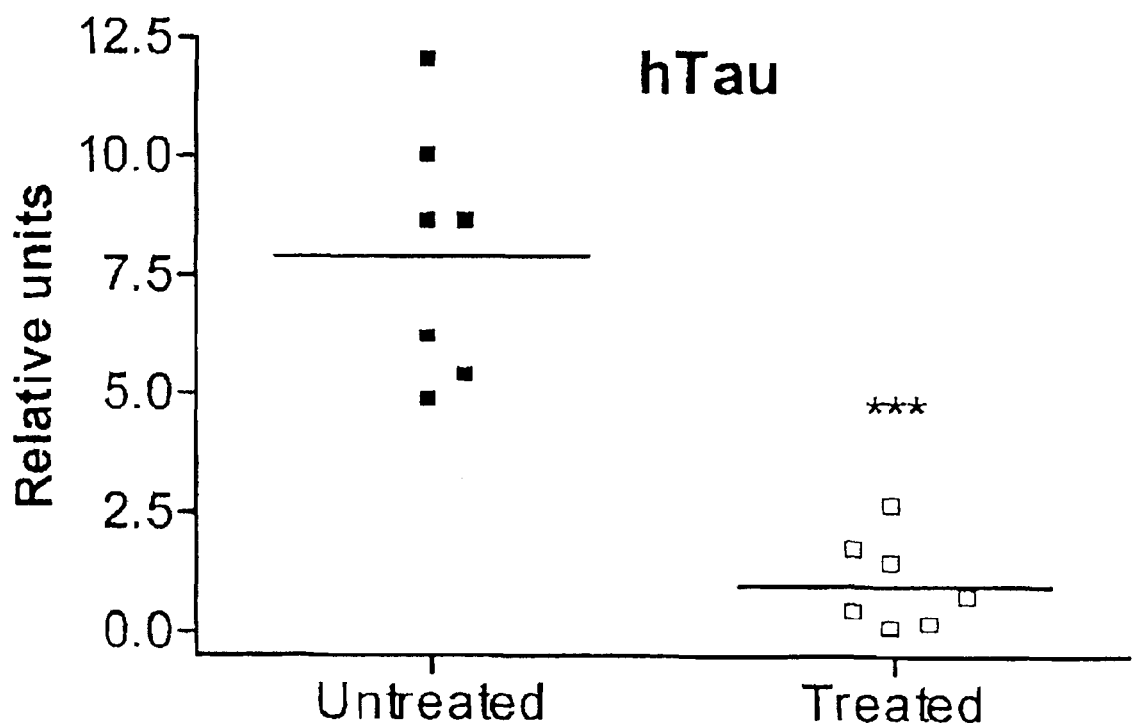
FIG. 14B shows the effect of one dose, short-term administration of PU-DZ8 on the levels of insoluble mutant tau in the JNPL3 mouse brain. Analysis of the insoluble tau (P3) fractions extracted from the subcortical brain region of 6-month old mice treated with PU-DZ8 (75 mg/kg) for 4, 8, 12 and 24 h is presented.

FIG. 14A. shows the effects of one dose, short term administration of PU-DZ8 on the levels of soluble mutant tau in the JNPL3 mouse brain The subcortical brain region of 2.5 to 4-month old mice is presented. Human Tau levels were normalized to those of Hsp90. FIG. 14B shows the effect of one dose, short-term administration of PU-DZ8 on the levels of insoluble mutant tau in the JNPL3 mouse brain. Analysis of the insoluble tau (P3) fractions extracted from the subcortical brain region of 6-month old mice treated with PU-DZ8 (75 mg/kg) for 4, 8, 12 and 24 h is presented Example 13

To investigate whether modulation of mTau could be sustained over a longer Hsp90 inhibitor-treatment period, without being toxic to mice, JNPL3 mice were subjected for 30 days to these agents. Female JNPL3 mice 6.5 months of age (n=10) were administered i.p. vehicle (n=5) or one of the Hsp90 inhibitors, PU24FC1 (200 mg/kg) or PU-DZ8 (75 mg/kg) (n=5), on a daily, five-times per week schedule and animals were sacrificed at 8 h following the last administered dose of inhibitor. No toxicity was observed as evidenced by lack of significant change in animal weight, fur appearance, appetite and posture. Furthermore, no visible internal organ damage was detected at sacrifice upon gross inspection. Both S1 and P3 fractions extracted from the subcortical brain region of these mice were analyzed for mTau expression and phosphorylation. A significant reduction in Tau expression and phosphorylation in both the precursor protein pool (S1 fraction) (hTau, P<0.0001) and the toxic aggregate (P3 fraction) (phosphorylated Tau at T231, P=0.0034) (FIG. 15), as well as p35 reduction in S1 fraction was observed in mice treated with the Hsp90 inhibitor.

Collectively, the rapid kinetics of Tau degradation in both the soluble pool and the aggregated form by the Hsp90 inhibitors suggests that Hsp90 regulates the toxic Tau aggregate and facilitates its formation and accumulation. These data also suggest that an Hsp90 inhibitor may be used in the treatment of tauopathies both to prevent the formation of toxic aggregates and to solubilize the already aggregated toxic tau.

Figure 15:
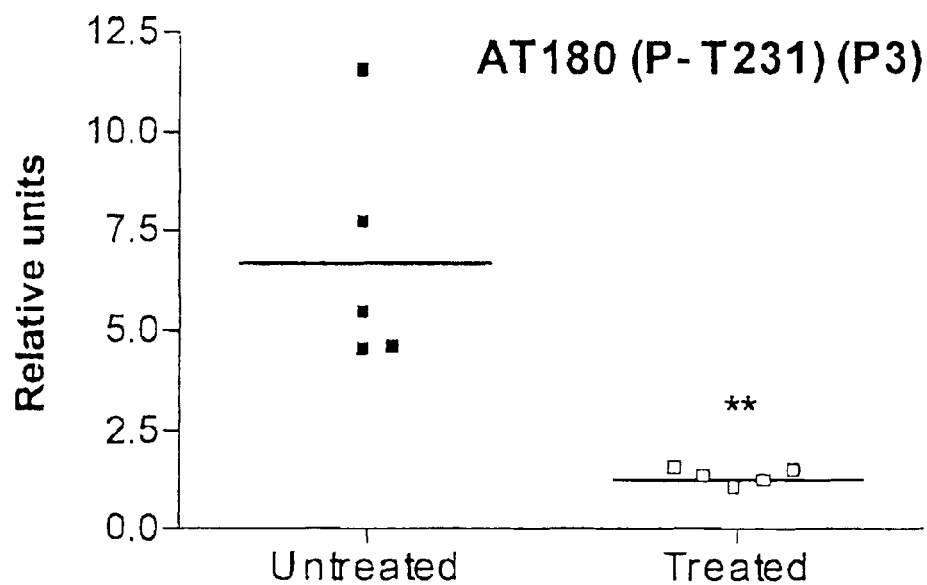
FIG. 15 shows the effect of long term PU-DZ8 administration on hyperphosphorylated tau in toxic tau aggregates.

FIG. 15 shows the effect of long term PU-DZ8 administration on hyperphosphorylated tau in toxic tau aggregates.

Example 14

In tauopathies transformation is characterized by abnormalities in the Tau protein leading to an accumulation of hyperphosphorylated and aggregated Tau (5-7). In Alzheimer's disease (AD), Tau hyperphosphorylation is suggested to be a pathogenic process caused by aberrant activation of several kinases, in particular cyclin-dependent protein kinase 5 (cdk5) and glycogen synthase kinase-3 beta (gsk3 β, leading to phosphorylation of Tau on pathogenic sites. Hyperphosphorylated Tau in AD is believed to misfold, undergo net dissociation from microtubules and form toxic Tau aggregates (9, 10). Phosphorylation of Tau by cdk5 is initiated through activation by complex formation with one of the neuron-specific proteins p35 or p39 (22, 23). However, only suppression of p35 by antisense oligonucleotide treatment, and not of the highly related isoform p39, selectively reduces cdk5 activity (24). In addition, levels of p35 but not cdk5 protein are rate-limiting for cdk5 activity (25). In concordance, we assessed the influence of Hsp90 inhibition on p35 expression.

We detected a dose- and time-dependent degradation of p35 by PU24FC1 in primary neurons, as well as in COS-7/p35 and COS-7/p35/Tau cells. Embryonic primary rat cortical neurons and COS-7 cells transfected with cDNAs corresponding to either p35 alone (COS-7/p35) or both p35 and Tau (COS-7/p35/Tau) are cellular systems that enable the evaluation of these inhibitors on cdk5/p35 activity and stability and also on Tau phosphorylation at putative cdk5 sites. These are relevant experimental systems to study aberrant neuronal kinase activity because phosphorylation of Tau at these sites is enhanced in embryonic and juvenile brains (20) and is similar to AD afflicted brains (21). In addition, COS-7 cells transfected with the cdk5 activator p35 express Tau phosphorylated at pathogenic sites (21). Effects were seen at approximately 1-5 μM PU24FC1 and were maximal at 10 μM Hsp90 inhibitor, in agreement with the affinity of this compound for Hsp90. Exogenously introduced p35 was more sensitive to Hsp90 inhibition than the endogenous protein, suggesting that by analogy to Hsp90 oncoproteins, buffering and stabilization of aberrant proteins in tauopathy may be accomplished by co-opting Hsp90. Reduction of p35 levels by Hsp90 inhibition affected the activity of the cdk5/p35 complex, as measured using a substrate of cdk5, the histone-H1.

To investigate whether decreased p35 expression resulted in reduced phosphorylation of Tau, we measured Tau phosphorylation on three putative cdk5 sites, namely S202/T205, T231 and T181 (26, 27). These sites have been shown to be abnormally phosphorylated in AD brains (28). PU24FC1 lessened phosphorylation on these sites in a dose-dependent manner without affecting normal Tau protein expression. As observed for p35 levels and activity, effects were evident at 5 μM and maximal at 10 μM inhibitor. In addition, the kinetics of p35 degradation were similar to those observed for reduction in Tau phosphorylation.

To investigate the in vivo effect of Hsp90 inhibition on p35 in a WT Tau environment, we made use of hTau mice (41). hTau mice develop Tau pathology with a distribution that is comparable to that occurring in the early stages of AD. The majority of Tau pathology in hTau mice is located in the cortical brain region. These mice express six isoforms of non-mutant human Tau, but develop AD-like Tau-pathology. Heat-stable fractions (S1) prepared from cortical homogenates of these mice indicate an age-related accumulation of Tau phosphorylated at putative cdk5 sites. We examined whether inhibition of Hsp90 in these brains may lead to a reduction in p35 expression and a consequent alleviation of Tau phosphorylation. hTau female mice (n=10) 4 and 8-10 months of age were administered either vehicle or one dose of PU-DZ8 (75 mg/kg) i.p. and animals were sacrificed at 4 h or 8 h post-administration. Aggregate-free Tau (S1) fractions were prepared from the cortical region of these mice and human Tau levels assessed by immunobloting with an antibody specific for 3-repeat domain Tau (RD3). By analogy to experiments on primary neuronal cultures and WT Tau transfected cells, the Hsp90 inhibitor had no effect on soluble WT Tau expression. However, both a significant time-dependent reduction in p35 levels (P=0.0019) (FIG. 16A) and alleviation of Tau phosphorylation on Ser202, as detected by antibody CP13 (P=0.0078), were evident at 8 h post-administration of the Hsp90 inhibitor (FIG. 16B). The monoclonal antibody CP13 is commonly used to detect Tau pathology in both early and more advanced stages of Tau aggregate accumulation (41). Collectively, these data position p35/cdk5 as a kinase complex prone to aberrantly phosphorylate WT and mutant Tau, and suggest Hsp90 as a regulator of its activity in both Tau environments.

Figure 16A:
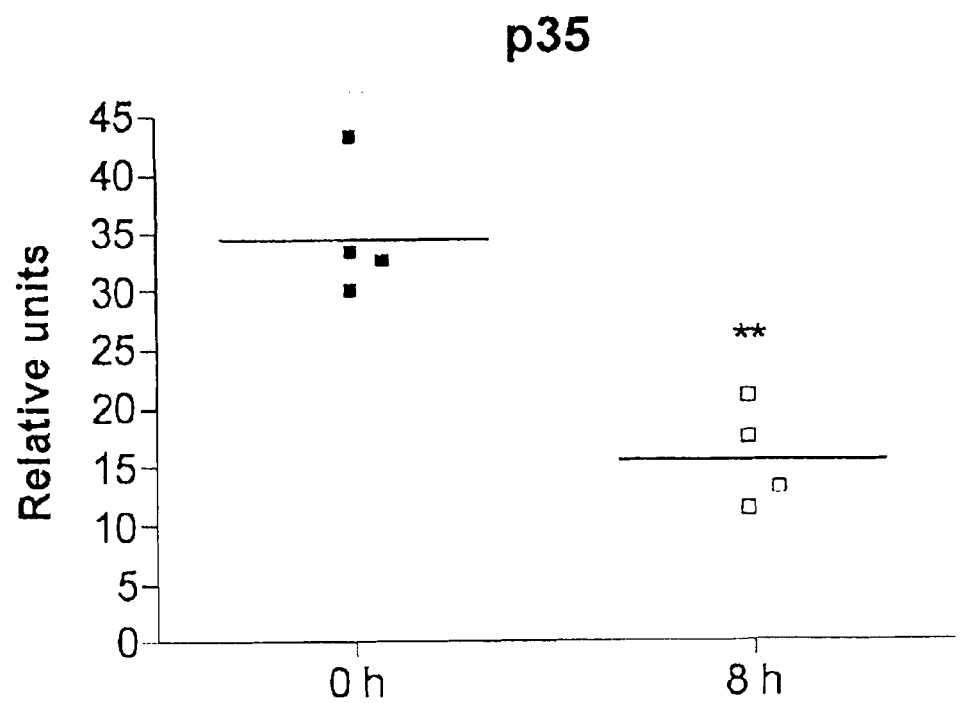
FIG. 16A shows the effect of PU-DZ8 on p35 in the htau mice that express pathogenically hyperphosphorylated WT tau similarly to Alzheimer's patients
Figure 16B:
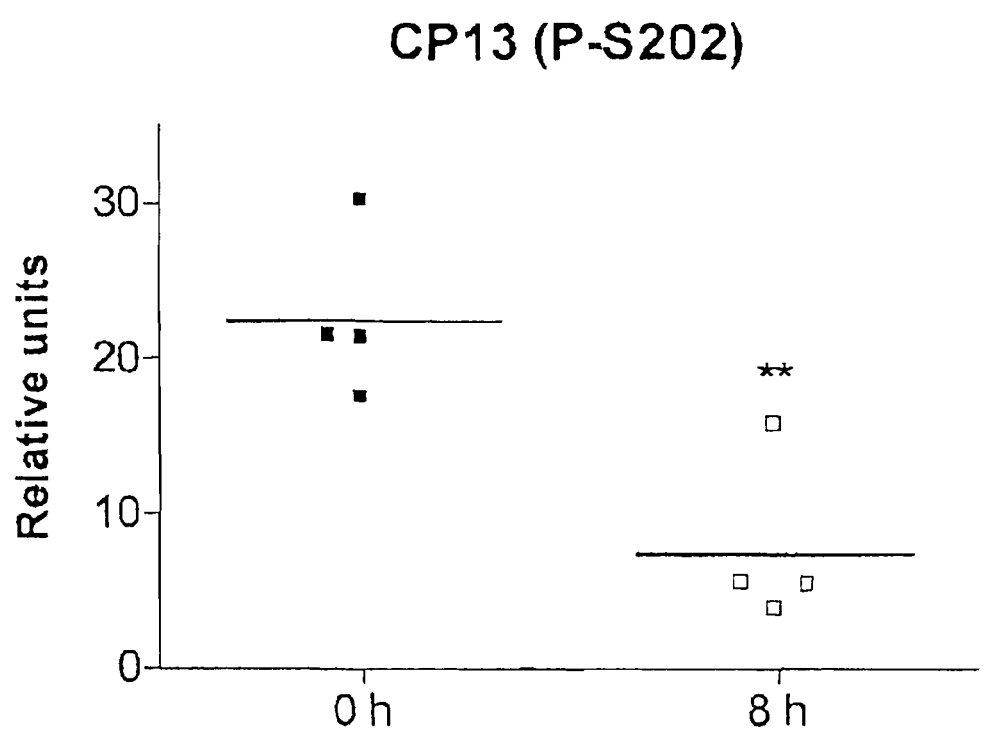
FIG. 16B shows the effect of PU-DZ8 tau phosphorylation in the htau mice that express pathogenically hyperphosphorylated WT tau similarly to Alzheimer's patients

FIG. 16A shows the effect of PU-DZ8 on p35 in the htau mice that express pathogenically hyperphosphorylated WT tau similarly to Alzheimer's patients. FIG. 16B shows the effect of PU-DZ8 tau phosphorylation in the htau mice that express pathogenically hyperphosphorylated WT tau similarly to Alzheimer's patients.

REFERENCES

The following references are cited herein, and are incorporated herein by reference in their entirety.

1. He H, Llauger L, Rosen N, Chiosis G. General Method for the Synthesis of 8-Arylsulfanyl Adenine Derivatives, J. Org. Chem. 2004, 69, 3230-3232.
2. He H, Zatorska D, Kim J, Aguirre J, Llauger L, She Y, Wu N, Immormino R M, Gewirth D T, Chiosis G. Identification of Potent Water-Soluble Purine-Scaffold Inhibitors of the Heat Shock Protein 90. J. Med. Chem. 2006, 49(1):381-90.
3. Soti C, Csermely P. Chaperones and aging: role in neurodegeneration and in other civilizational diseases. Neurochem Int. 2002 December; 41(6):383-9.
4. Poletti A, Negri-Cesi P, Martini L. Endocrine. 2005 December; 28(3):243-62.
5. Beglopoulos V, Shen J. Trends Pharmacol Sci. 2006 January; 27(1):33-40.
6. Sorger P K. Heat shock factor and the heat shock response. Cell. 1991 May 3; 65(3):363-6.
7. Zou J, Guo Y, Guettouche T, Smith D F, Voellmy R. Repression of heat shock transcription factor HSF1 activation by HSP90 (HSP90 complex) that forms a stress-sensitive complex with HSF1. Cell. 1998 Aug. 21; 94(4):471-80.
8. Morimoto R I, Santoro M G. Stress-inducible responses and heat shock proteins: new pharmacologic targets for cytoprotection. Nat Biotechnol. 1998 September; 16(9):833-8.,
9. Gardian G, Vecsei L. Huntington's disease: pathomechanism and therapeutic perspectives. J Neural Transm. 2004 October; 111(10-11):1485-94.
10. Rajgopal Y, Vemuri M C. Ethanol induced changes in cyclin-dependent kinase-5 activity and its activators, P35, P67 (Munc-18) in rat brain. Neurosci Lett. 2001 Aug. 10; 308(3):173-6.
11. Patrick G N, Zukerberg L, Nikolic M, de la Monte S, Dikkes P, Tsai L H. Conversion of p35 to p25 deregulates Cdk5 activity and promotes neurodegeneration. Nature. 1999 Dec. 9; 402(6762):615-22.
12. Dou F, Netzer W J, Tanemura K, Li F, Hartl F U, Takashima A, Gouras G K, Greengard P, Xu H. Chaperones increase association of tau protein with microtubules. Proc Natl Acad Sci USA. 2003 Jan. 21; 100(2):721-6.
13. Nakamura S, Kawamoto Y, Nakano S, Ikemoto A, Akiguchi I, Kimura J. Cyclin-dependent kinase 5 in Lewy body-like inclusions in anterior horn cells of a patient with sporadic amyotrophic lateral sclerosis. Neurology. 1997 January; 48(1):267-70.
14. Bajaj N P, Al-Sarraj S T, Anderson V, Kibble M, Leigh N, Miller C C. Cyclin-dependent kinase-5 is associated with lipofuscin in motor neurones in amyotrophic lateral sclerosis. Neurosci Lett. 1998 Mar. 27; 245(1):45-8.
15. Wang J, Liu S, Fu Y, Wang J H, Lu Y. Cdk5 activation induces hippocampal CA1 cell death by directly phosphorylating NMDA receptors. Nat Neurosci. 2003 October; 6(10):1039-47.
16. Sittler A, Lurz R, Lueder G, Priller J, Lehrach H, Hayer-Hartl M K, Hartl F U, Wanker E E. Geldanamycin activates a heat shock response and inhibits huntingtin aggregation in a cell culture model of Huntington's disease. Hum Mol Genet. 2001 Jun. 1; 10(12):1307-15.
17. Winklhofer K F, Reintjes A, Hoener M C, Voellmy R, Tatzelt J. Geldanamycin restores a defective heat shock response in vivo. J Biol Chem. 2001 Nov. 30; 276(48):45160-7.
18. Tatzelt J, Zuo J, Voellmy R, Scott M, Hartl U, Prusiner S B, Welch W J. Scrapie prions selectively modify the stress response in neuroblastoma cells. Proc Natl Acad Sci U S A. 1995 Mar. 28; 92(7):2944-8.
19. Auluck P K, Bonini N M. Pharmacological prevention of Parkinson disease in Drosophila. Nat Med. 2002 November; 8(11):1185-6.
20. Weishaupt J H, Kussmaul L, Grotsch P, Heckel A, Rohde G, Romig H, Bahr M, Gillardon F. Inhibition of CDK5 is protective in necrotic and apoptotic paradigms of neuronal cell death and prevents mitochondrial dysfunction. Mol Cell Neurosci. 2003 October; 24(2):489-502.
21. Bibb J A, Chen J, Taylor J R, Svenningsson P, Nishi A, Snyder G L, Yan Z, Sagawa Z K, Ouimet C C, Nairn A C, Nestler E J, Greengard P. Effects of chronic exposure to cocaine are regulated by the neuronal protein Cdk5. Nature. 2001 Mar. 15; 410(6826):376-80.
22. Brion J P, Couck A M. Cortical and brainstem-type Lewy bodies are immunoreactive for the cyclin-dependent kinase 5. Am J Pathol. 1995 November; 147(5):1465-76.
23. Chen J, Zhang Y, Kelz M B, Steffen C, Ang E S, Zeng L, Nestler E J. Induction of cyclin-dependent kinase 5 in the hippocampus by chronic electroconvulsive seizures: role of [Delta]FosB. J Neurosci. 2000 Dec. 15; 20(24):8965-71.
24. Sisodiya S M, Thom M, Lin W R, Bajaj N P, Cross J H, Harding B N. Abnormal expression of cdk5 in focal cortical dysplasia in humans. Neurosci Lett. 2002 Aug. 16; 328(3):217-20.
25. Green S L, Vulliet P R, Pinter M J, Cork L C. Alterations in cyclin-dependent protein kinase 5 (CDK5) protein levels, activity and immunocytochemistry in canine motor neuron disease. J Neuropathol Exp Neurol. 1998 November; 57(11):1070-7.
26. Nakano S, Akiguchi I, Nakamura S, Satoi H, Kawashima S, Kimura Aberrant expression of cyclin-dependent kinase 5 in inclusion body myositis. Neurology. 1999 Nov. 10; 53(8):1671-6.
27. Nakamura S, Kawamoto Y, Nakano S, Akiguchi I, Kimura J. Cyclin-dependent kinase 5 and mitogen-activated protein kinase in glial cytoplasmic inclusions in multiple system atrophy. J Neuropathol Exp Neurol. 1998 July; 57(7):690-8.
28. Honjyo Y, Kawamoto Y, Nakamura S, Nakano S, Akiguchi I. P39 immunoreactivity in glial cytoplasmic inclusions in brains with multiple system atrophy. Acta Neuropathol (Berl). 2001 March; 101(3):190-4.
30. E. Mandelkow and E.-M. Mandelkow, Kinesin motors and disease. Trends Cell Biol. 12 (2002), pp. 585-591.
31. Hong M, Trojanowski J Q, Lee V M Y. Tau-based neurofibrillary lesions. In: Clark C M, Trojanowski J Q, eds. Neurodegenerative dementia: clinical features and pathological mechanisms. New York: McGraw-Hill, 2000; 161-175.
32. von Bergen, M., Barghorn, S., Li, L., Marx, A., Biernat, J., Mandelkow, E. M. & Mandelkow, E. Mutations of tau protein in frontotemporal dementia promote aggregation of paired helical filaments by enhancing local beta-structure. (2001) J. Biol. Chem. 276, 48165-48174
33. Lee, V. M., Goedert, M. & Trojanowski, J. Q. Neurodegenerative tauopathies (2001) Annu. Rev. Neurosci. 24, 1121-1159
34. Matsumura, N., Yamazaki, T. & Ihara, Y. Stable expression in Chinese hamster ovary cells of mutated tau genes causing frontotemporal dementia and parkinsonism linked to chromosome 17 (FTDP-17). (1999) Am. J. Pathol. 154(6):1649-56.
35. Fath, T., Eidenmuller, J., and Brandt, R. Tau-mediated cytotoxicity in a pseudohyperphosphorylation model of Alzheimer's disease (2002) J Neurosci 22, 9733-9741.
36. Ahlijanian, M. K., Barrezueta, N. X., Williams, R. D., Jakowski, A., Kowsz, K. P., McCarthy, S., Coskran, T., Carlo, A., Seymour, P. A., Burkhardt, J. E., Nelson, R. B., and McNeish, J. D. Hyperphosphorylated tau and neurofilament and cytoskeletal disruptions in mice overexpressing human p25, an activator of cdk5. (2000) Proc Natl Acad Sci USA 97, 2910-2915.
37. Noble, W., Olm, V., Takata, K., Casey, E., Mary, O., Meyerson, J., Gaynor, K., LaFrancois, J., Wang, L., Kondo, T., Davies, P., Burns, M., Veeranna, Nixon, R., Dickson, D., Matsuoka, Y., Ahlijanian, M., Lau, L. F., and Duff, K. Cdk5 is a key factor in tau aggregation and tangle formation in vivo. (2003) Neuron 38, 555-565.
38. Lucas, J. J., Hernandez, F., Gomez-Ramos, P., Moran, M. A., Hen, R., and Avila, J. Decreased nuclear beta-catenin, tau hyperphosphorylation and neurodegeneration in GSK-3beta conditional transgenic mice. (2001) Embo J 20, 27-39.
39. Tsai, L. H., Takahashi, T., Caviness, V. & Harlow, E. (1993) Activity and expression patterns of cyclin-dependent kinase 5 in the embryonic mouse nervous system. Development 119, 1029-1040.
40. Paudel, H. K., Lew, J., Ali, Z. & Wang, J. (1993) Brain proline-directed protein kinase phosphorylates tau on sites that are abnormally phosphorylated in tau associated with Alzheimer's paired helical filaments. J. Biol. Chem. 268, 23512-23518.
41. Lazaro, J. B., Kitzman, M., Poul, M. A., Vandromme, M., Lamb, N. Y. & Fernandez, A. (1997) Cdk5, is a positive regulator of myogenesis in mouse C2 cells. J. Cell Sci. 110, 1251-1260.
42. Alvarez, A., Toro, R., Caceres, A. & Maccioni, R. B. (1999) Inhibition of tau phosphorylating protein kinase Cdk5 prevents beta-amyloid induced neuronal death. FEBS Lett. 459, 421-426.
43. Maccioni R B, Otth C, Concha I I, Munoz J P. The protein kinase Cdk5. Structural aspects, roles in neurogenesis and involvement in Alzheimer's pathology. Eur J Biochem. 2001 March; 268(6):1518-27
44. Walling A D. Amyotrophic lateral sclerosis: Lou Gehrig's disease. Am Fam Physician. 1999 Mar. 15; 59(6):1489-96.
45. Julien J P, Beaulieu J M. Cytoskeletal abnormalities in amyotrophic lateral sclerosis: beneficial or detrimental effects, J Neurol Sci. 2000 Nov. 1; 180(1-2):7-14.
47. Julien J P, Couillard-Despres S, Meier J. Transgenic mice in the study of ALS: the role of neurofilaments. Brain Pathol. 1998 October; 8(4):759-69.
48. Fahn S. Description of Parkinson's disease as a clinical syndrome. Ann N Y Acad Sci. 2003 June; 991:1-14.
49. Neystat M, Rzhetskaya M, Oo T F, Kholodilov N, Yarygina O, Wilson A, El-Khodor BF, Burke R E. Expression of cyclin-dependent kinase 5 and its activator p35 in models of induced apoptotic death in neurons of the substantia nigra in vivo. J Neurochem. 2001 June; 77(6):1611-25.
50. Kanemaru K, Takio K, Miura R, Titani K, Ihara Y. Fetal-type phosphorylation of the tau in paired helical filaments. J Neurochem. 1992 May; 58(5):1667-75.
51. Stoothoff W H, Johnson G V. Tau phosphorylation: physiological and pathological consequences. Biochim Biophys Acta. 2005 Jan. 3; 1739(2-3):280-97.
52. Michel G, Mercken M, Murayama M, Noguchi K, Ishiguro K, Imahori K, Takashima A. Characterization of tau phosphorylation in glycogen synthase kinase-3beta and cyclin dependent kinase-5 activator (p23) transfected cells. Biochim Biophys Acta. 1998 Apr. 10; 1380(2):177-82.
53. Stancato L F, Silverstein A M, Owens-Grillo J K, Chow Y H, Jove R, Pratt W B. The hsp90-binding antibiotic geldanamycin decreases Raf levels and epidermal growth factor signaling without disrupting formation of signaling complexes or reducing the specific enzymatic activity of Raf kinase. J Biol Chem 1997; 272:4013-20.
54. Donze O, Abbas-Terki T, Picard D. The Hsp90 chaperone complex is both a facilitator and a repressor of the dsRNA-dependent kinase PKR. Embo J 2001; 20:3771-80.
55. Cadepond F, Schweizer-Groyer G, Segard-Maurel I, Jibard N, Hollenberg S M, Giguere V, et al. Heat shock protein 90 as a critical factor in maintaining glucocorticosteroid receptor in a nonfunctional state. J Biol Chem 1991; 266:5834-41.
56. Oshima, T., Ward, J. M., Huh, C. G., Longenecker, G., Veeranna, C., Pant, H. C., Brady, R. O., Martin, L. J. & Kulkami, A. B. (1996) Targeted disruption of the cyclin-dependent kinase 5 gene results in abnormal corticogenesis, neuronal pathology and perinathan death. Proc. Natl. Acad. Sci. USA 93, 11173 11178.
57. Chae, T., Kwon, Y. T., Bronson, R., Dikkes, P., Li, E. & Tsai, L. H. (1997) Mice lacking p35, a neuronal specific activator of Cdk5 display cortical lamination defects, seizures, and adult lethality. Neuron 18, 29-42.
58. Lee K Y, Clark A W, Rosales J L, Chapman K, Fung T, Johnston R N. Elevated neuronal Cdc2-like kinase activity in the Alzheimer disease brain. Neurosci Res. 1999 May; 34(1):21-9.
59. Lewis J, McGowan E, Rockwood J, Melrose H, Nacharaju P, Van Slegtenhorst M, Gwinn-Hardy K, Paul Murphy M, Baker M, Yu X, Duff K, Hardy J, Corral A, Lin WL, Yen S H, Dickson D W, Davies P, Hutton M. Neurofibrillary tangles, amyotrophy and progressive motor disturbance in mice expressing mutant (P301L) tau protein. Nat Genet. 2000 August; 25(4):402-5.
60. Hutton M, Lendon C L, Rizzu P, Baker M, Froelich S, Houlden H, Pickering-Brown S, Chakraverty S, Isaacs A, Grover A, Hackett J, Adamson J, Lincoln S, Dickson D, Davies P, Petersen R C, Stevens M, de Graaff E, Wauters E, van Baren J, Hillebrand M, Joosse M, Kwon J M, Nowotny P, Che L K, Norton J, Morris J C, Reed L A, Trojanowski J, Basun H, Lannfelt L, Neystat M, Fahn S, Dark F, Tannenberg T, Dodd P R, Hayward N, Kwok J B, Schofield P R, Andreadis A, Snowden J, Craufurd D, Neary D, Owen F, Oostra B A, Hardy J, Goate A, van Swieten J, Mann D, Lynch T, Heutink P. Association of missense and 5'-splice-site mutations in tau with the inherited dementia FTDP-17. Nature. 1998 Jun. 18; 393 (6686):702-5.

61. Poorkaj P, Bird T D, Wijsman E, Nemens E, Garruto R M, Anderson L, Andreadis A, Wiederholt W C, Raskind M, Schellenberg G D. Tau is a candidate gene for chromosome 17 frontotemporal dementia. Ann Neurol. 1998 June; 43(6):815-25.

62. Sahara N, Lewis J, DeTure M, McGowan E, Dickson D W, Hutton M, Yen S H. Assembly of tau in transgenic animals expressing P301L tau: alteration of phosphorylation and solubility. J Neurochem. 2002 December; 83(6):1498-1508.

63. Lewis J., Dickson D. W., Lin W.-L., Chisholm L., Corral A., Jones G., Yen S.-H., Sahara N., Skipper L., Yager D., Eckman C., Hardy J., Hutton M. and McGrowan E. (2001) Enhanced neurofibrillary degeneration in transgenic mice expressing mutant tau and APP. Science 293, 1487-1491.

64. Tatebayashi Y, Miyasaka T, Chui D H, Akagi T, Mishima K, Iwasaki K, Fujiwara M, Tanemura K, Murayama M, Ishiguro K, Planel E, Sato S, Hashikawa T, Takashima A. Tau filament formation and associative memory deficit in aged mice expressing mutant (R406W) human tau. Proc Natl Acad Sci USA. 2002 Oct. 15; 99(21):13896-901.

65. Gotz J, Chen F, van Dorpe J, Nitsch R M. Formation of neurofibrillary tangles in P301l tau transgenic mice induced by Abeta 42 fibrils. Science. 2001 Aug. 24; 293 (5534): 1491-5.

66. Kim J, Felts S, He H, Llauger L, Huezo H, Rosen N, Chiosis G. Development of a fluorescence polarization assay for the molecular chaperone Hsp90. J. Biomolecular Screening 2004, 9(5):375-81.

67. Llauger L, Felts S, Huezo H, Rosen N, Chiosis G. Synthesis of novel fluorescent probes for the molecular chaperone Hsp90. Bioorg. Med. Chem. Lett. 2003, 13, 3975-3978.

68. Moulick K, Clement C C, Aguirre J, Kim J, Kang Y, Felts S, Chiosis G. Synthesis of a red-shifted fluorescence polarization probe for Hsp90. Bioorg. Med. Chem. Lett. Available online 22 Jun. 2006.

69. Huezo H, Vilenchik M, Rosen N, Chiosis G. Microtiter cell-based assay for the detection of agents that alter cellular levels of Her2 and EGFR. Chem Biol. 2003, 10(7), 629-634.

70. Ferrer I, Gomez-Isla T, Puig B, Freixes M, Ribe E, Dalfo E, Avila J. Current advances on different kinases involved in tau phosphorylation, and implications in Alzheimer's disease and tauopathies. Curr Alzheimer Res. 2005 January; 2(1):3-18.

71. Fu W Y, Fu A K, Lok K C, Ip F C, Ip N Y. Induction of Cdk5 activity in rat skeletal muscle after nerve injury. Neuroreport. 2002 Feb. 11; 13(2):243-7.

77. Greenberg, S. G., and Davies, P. (1990) Proc. Natl. Acad. Sci. USA 87, 5827-5831.

89. Hansch C, Leo A J. Substituent constant for correlation analysis in chemistry and biology. New York: Wiley, 1979.

90. Hansch C, Bjorkroth J, Leo A J. Hydrophobicity and central nervous system agents: on the principle of minimal hydrophobicity in drug design. Pharm Sci 76: 663, 1987.

91. Österberg T, Norinder U. Prediction of polar surface area and drug transport processes using simple parameters and PLS statistics. J Chem Inf Comput Sci 40: 1408-1411, 2000.

92. Feng R M. Assessment of blood-brain barrier penetration: in silico, in vitro and in vivo. Curr Drug Metab 3: 647-657, 2002.

93. Skaaeda T, Okamura N, Nagata S, Yagami T, Horinouchi M, Okumura K, Yamahita F, Hashida M. Molecular and pharmacokinetic properties of 222 commercially available oral drugs in humans. Biol Pharm Bull 24: 935-940, 2001.

94. Abraham M H, Chadha H S, Martins F, Mitchell R C, Bradbury M W, Gratton J A. Hydrogen bonding part 46: a review of the correlation and prediction of transport properties by an LFER method: physicochemical properties brain penetration and skin permeability. Pestic Sci 55: 78-88, 1999.

95. Kelder J, Grootenhuis P D J, Bayada D M, Delbressine L P C, Ploemen J-P. Polar molecular surface as a dominating determinant for oral absorption and brain penetration of drugs. Pharm Res 16: 1514-1519, 1999.

96. van de Waterbeemd H, Camenish G, Folkers G, Chretien J R, Raevsky O A. Estimation of blood-brain barrier crossing of drugs using molecular size and shape, and H-bonding characteristics. J Drug Target 6: 151-165, 1998.

97. P. Ertl, B. Rohde, P. Selzer, Fast calculation of molecular polar surface area as a sum of fragment-based contributions and its application to the prediction of drug transport properties. J. Med. Chem. 43, 3714-3717 (2000).

98. C. A. Lipinski, F. Lombardo, B. W. Dominy, P. J. Feeney, Experimental and computational approaches to estimate solubility and permeability in drug discovery and development settings. Adv. Drug. Delivery Rev. 23, 4-25 (1997).

99. D. F. Veber, S. R. Johnson, H.-Y. Cheng, B. R. Smith, K. W. Ward, K. D. Kopple, Molecular properties that influence the oral bioavailability of drug candidates. J. Med. Chem. 45, 2615-2623 (2002).

100. Clark D E. In silico prediction of blood-brain barrier permeation, Drug Discovery Today 8: 927-933, 2003.

101. Lin J H, Rodrigues A D. In vitro model for early studies of drug metabolism. In: Pharmacokinetics optimization in drug research: biological, physicochemical and computational strategies (Testa, Van de Waterbeemed H, Folker G, Guy R, eds.), pp 217-243. New York: Wiley-VCH, 2001.

102. Raub J T. Early preclinical evaluation in support of hit identification and lead optimization for brain exposure. AAPS Workshop on Optimization of Drug-Like Properties During Lead Optimization. Parsippany, N.J., 19-22 September, 2004.

103. Klettner A. The induction of heat shock proteins as a potential strategy to treat neurodegenerative disorders. Drug News Perspect. 2004 June; 17(5):299-306.

104. Barral J M, Broadley S A, Schaffar G, Hartl F U. Roles of molecular chaperones in protein misfolding diseases. Semin Cell Dev Biol. 2004 February; 15(1):17-29.

105. Xu H., Gouras G K, Greenfield J P, Vincent B, Naslund J, Mazzarellu L, Fired G, Jovanovic J N, Seeger M, Relkin N R et al, (1998) Nat. Ned. 4: 447-451.

106. Lamphere L, Fiore F, Xu X, Brizuela L, Keezer S, Sardet C, Draetta G F, Gyuris J (1997) Oncogene 14:1999-2004.

The invention claimed is:
1. A method for treatment of neurodegenerative disease, comprising administering to an individual in need of such treatment a therapeutically effective amount of a compound having structure:

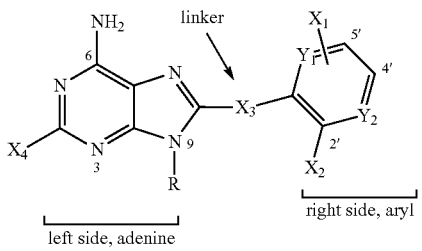

left side, adenine | right side, aryl wherein R is hydrogen, or a $C_1$ to $C_{10}$ alkyl, $C_2$ to $C_{10}$ alkynyl, or $C_2$ to $C_{10}$ alkoxyalkyl group, optionally including heteroatoms;

$Y_1$ and $Y_2$ are independently C or N;

$X_4$ is hydrogen or halogen;

$X_3$ is $CH_2$, $CF_2$, S, SO, $SO_2$, O, NH, or $NR^2$, wherein $R^2$ is alkyl; and $X_2$ is halogen, alkyl, halogenated alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, $SO_2$-alkyl, COO-alkylm $NH_2$, OH, or CN; and $X_1$ has the formula —X—Y—Z— wherein, X, Y and Z are independently C, N, S or O, connected by single or double bonds and with apoprriate hydrogen substitution to satisfy valence, or Y may be $(CH_2)_2$, wherein one of X and Z is bonded at the 5'-position to the aryl ring and the other is bonded to the 4'position, and wherein the compound is optionally in the form of an acid addition salt;

wherein the neurodegenerative disease is selected from the group consisting of complete androgen insensitivity syndrome (CAIS), spinal and bulbar muscular atrophy (SBMA or Kennedy's disease), Alzheimer's Disease (AD), sporadic frontotemporal dementia with parkinsonism (FTDP), familial FTDP-17 syndromes, Parkinson's disease, and Huntington disease.

2. The method of claim 1, wherein the compound and the mode of administration are selected such that the compound is delivered to the brain.

3. The method of claim 2, wherein at least one of X, Y and Z is a carbon atom.

4. The method of claim 3, wherein $X_1$ is —O—$(CH_2)_n$—O—, wherein n is 1 or 2.

5. The method of claim 1, wherein at least one of X, Y and Z is a carbon atom.

6. The method of claim 5, wherein $X_1$ is —O—$(CH_2)_n$—O—, wherein n is 1 or 2.

7. The method of claim 6, wherein $X_2$ is halogen.

8. The method of claim 7, wherein $X_2$ is Br or I.

9. The method of claim 6, wherein R is an alkyl group containing a nitrogen heteroatom.

10. The method of claim 9, wherein R is 3-isopropylaminopropyl, 3-(isopropyl(methyl)amino)propyl, 3-(isopropyl(ethyl)amino)propyl, 3-((2-hydroxyethyl)(isopropyl)amino)propyl, 3-(methyl(prop-2-ynyl)amino)propyl, 3-(allyl(methyl)amino)propyl, 3-(ethyl(methyl)amino)propyl, 3-(cyclopropyl(propyl)amino)propyl, 3-(cyclohexyl(2-hydroxyethyl)amino)propyl, 3-(2-methylaziridin-1-yl)propyl, 3-(piperidin-1-yl)propyl, 3-(4-(2-hydroxyethyl)piperazin-1-yl)propyl, 3-morpholinopropyl, 3-(trimethylammonio)propyl, 2-(isopropylamino)ethyl, 2-(isobutylamino)ethyl, 2-(neopentylamino)ethyl, 2-(cyclopropylmethylamino)ethyl, 2-(ethyl(methyl)amino)ethyl, 2-(isobutyl(methyl)amino)ethyl, or 2-(methyl(prop-2-ynyl)amino)ethyl.

11. The method of claim 10, wherein R is 3-(methyl(prop-2-ynyl)amino)propyl.

12. The method of claim 10, wherein R is 2-(isobutylamino)ethyl.

13. The method of claim 10, wherein R is 2-(neopentylamino)ethyl.

14. The method of claim 10, wherein R is 3-isopropylaminopropyl.

15. The method of claim 10, wherein $X_2$ is halogen.

16. The method of claim 15, wherein $X_2$ is Br or I.

17. The method of claim 6, wherein $X_4$ is halogen.

18. The method of claim 17, wherein $X_2$ is halogen.

19. The method of claim 18, wherein $X_2$ is Br or I.

20. The method of claim 17, wherein R is an alkyl group containing a nitrogen heteroatom.

21. The method of claim 20, wherein R is 3-isopropylaminopropyl, 3-(isopropyl(methyl)amino)propyl, 3-(isopropyl(ethyl)amino)propyl, 3-((2-hydroxyethyl)(isopropyl)amino)propyl, 3-(methyl(prop-2-ynyl)amino)propyl, 3-(allyl(methyl)amino)propyl, 3-(ethyl(methyl)amino)propyl, 3-(cyclopropyl(propyl)amino)propyl, 3-(cyclohexyl(2-hydroxyethyl)amino)propyl, 3-(2-methylaziridin-1-yl)propyl, 3-(piperidin-1-yl)propyl, 3-(4-(2-hydroxyethyl)piperazin-1-yl)propyl, 3-morpholinopropyl, 3-(trimethylammonio)propyl, 2-(isopropylamino)ethyl, 2-(isobutylamino)ethyl, 2-(neopentylamino)ethyl, 2-(cyclopropylmethylamino)ethyl, 2-(ethyl(methyl)amino)ethyl, 2-(isobutyl(methyl)amino)ethyl, or 2-(methyl(prop-2-ynyl)amino)ethyl.

22. The method of claim 20, wherein R is 3-(methyl(prop-2-ynyl)amino)propyl.

23. The method of claim 20, wherein R is 2-(isobutylamino)ethyl.

24. The method of claim 20, wherein R is 2-(neopentylamino)ethyl.

25. The method of claim 20, wherein R is 3-isopropylaminopropyl.

26. The method of claim 20, wherein $X_2$ is halogen.

27. The method of claim 26, wherein $X_2$ is Br or I.

28. The method of claim 4, wherein R is a terminal alkyne.

29. The method of claim 28, wherein R is propynyl.

30. The method of claim 29, wherein $X_2$ is halogen.

31. The method of claim 1, wherein the compound has the formula: PUDZ8

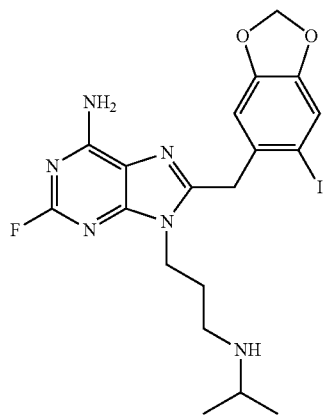 [SMILES: CC(C)NCCCn1c(Cc2cc3c(cc2I)OCO3)nc2c(N)nc(F)nc21]

or an acid addition salt thereof.

32. The method of claim 1, wherein the compound has the formula

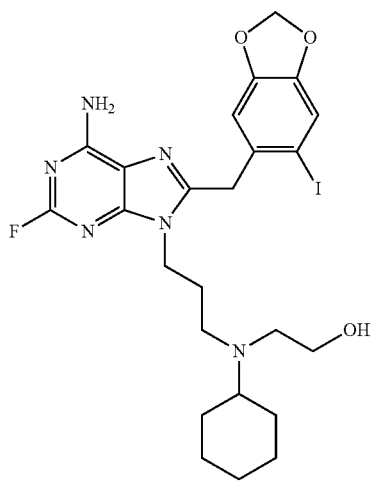 [SMILES: Nc1nc(F)nc2c1nc(Cc1cc3c(cc1I)OCO3)n2CCCN(CCO)C1CCCCC1]

or an acid addition salt thereof.

33. The method of claim 1, wherein the compound has the formula

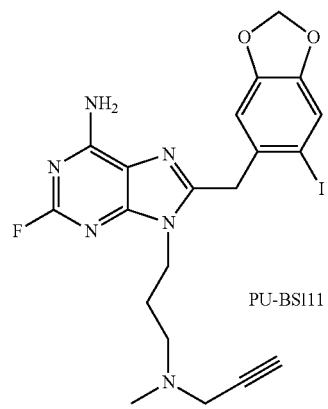 [SMILES: C#CCN(C)CCCn1c(Cc2cc3c(cc2I)OCO3)nc2c(N)nc(F)nc21]

or an acid addition salt thereof.

34. The method of claim 1, wherein the compound has the formula

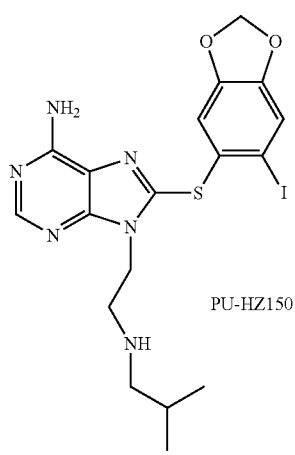 [SMILES: CC(C)CNCCn1c(Sc2cc3c(cc2I)OCO3)nc2c(N)ncnc21]

or an acid addition salt thereof.

35. The method of claim 1, wherein the compound has the formula

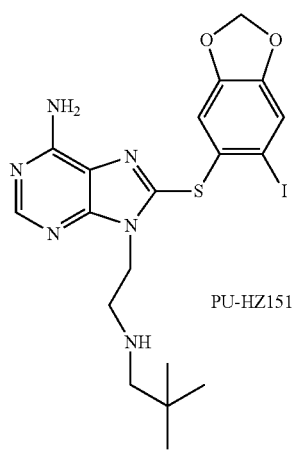 [SMILES: CC(C)(C)CNCCn1c(Sc2cc3c(cc2I)OCO3)nc2c(N)ncnc21]

or an acid addition salt thereof.

36. The method of claim 1, wherein the compound has the formula

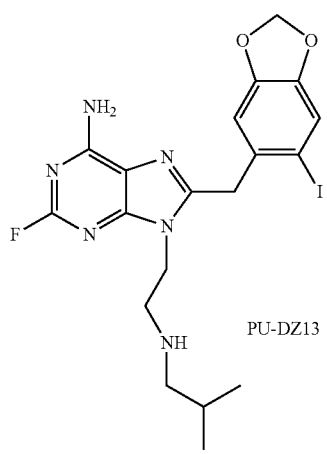 [SMILES: CC(C)CNCCn1c(Cc2cc3c(cc2I)OCO3)nc2c(N)nc(F)nc21]

or an acid addition salt thereof.

37. The method of claim 1, wherein the compound has the formula

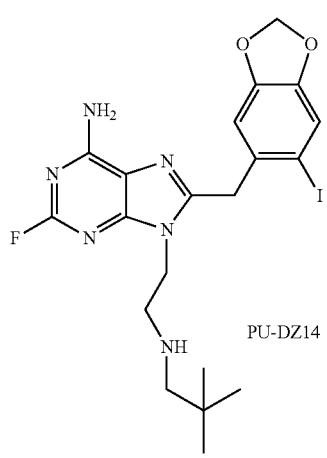 [SMILES: CC(C)(C)CNCCn1c(Cc2cc3c(cc2I)OCO3)nc2c(N)nc(F)nc21]

or an acid addition salt thereof.

38. The method of claim 4, wherein the compound crosses the blood brain barrier.

39. The method of claim 2, wherein the neurodegenerative disease is one in which aggregate, plaque or tangle formation occurs.

40. The method of claim 2, wherein the neurodegenerative disease is Alzheimer's Disease.

41. The method of claim 1, wherein the neurodegenerative disease is one in which aggregate, plaque or tangle formation occurs.

42. The method of claim 1, wherein the neurodegenerative disease is Alzheimer's Disease.

43. A compound:

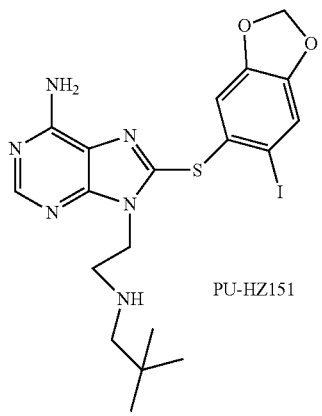 [SMILES: CC(C)(C)CNCCn1c(Sc2cc3c(cc2I)OCO3)nc2c(N)ncnc21]

PU-HZ151 or an acid addition salt thereof.

44. A method for treatment of a neurodegenerative disease, comprising administering to an individual in need of such treatment a therapeutically effective amount of a compound of claim 43; wherein the neurodegenerative disease is selected from the group consisting of complete androgen insensitivity syndrome (CAIS), spinal and bulbar muscular atrophy (SBMA of Kennedy's disease), Alzheimer's Disease (AD), sporadic frontotemporal dementia with parkinsonism (FTDP), familiar FTDP-17 syndromes, Parkinson's disease, and Huntington disease.

45. The method of claim 1, wherein the neurodegenerative disease is one that is characterized by abnormalities in a signaling pathway and/or by aberrant neuronal protein folding.

46. The method of claim 1, wherein the compound and the mode of administration are selected such that the compound is delivered to afflicted neurons characterized by the adnormalities in a signaling pathway and/pr by aberrant neuronal protein folding.

47. The method of claim 35, wherein the neurodegenerative disease Alzheimer's Disease (AD).

* * * * *

UNITED STATES PATENT AND TRADEMARK OFFICE
CERTIFICATE OF CORRECTION

PATENT NO. : 10,336,757 B2
APPLICATION NO. : 12/307063
DATED : July 2, 2019
INVENTOR(S) : Chiosis et al.

Page 1 of 2

It is certified that error appears in the above-identified patent and that said Letters Patent is hereby corrected as shown below:

In the Specification

Column 1, Line 13, delete:
"This invention was supported in part by NIH grant AG096464. The United States government may have certain rights in this invention."
And insert:
--This invention was made with government support under AG009464 awarded by the National Institutes of Health. The government has certain rights in the invention.--

In the Claims

In Claim 1, Column 31, beginning at Line 13 and ending at Line 14, please delete:
"wherein R is hydrogen, or a $C_1$ to $C_{10}$ alkyl, $C_2$ to $C_{10}$ alkynyl,"
And insert:
--wherein R is hydrogen, or a $C_1$ to $C_{10}$ alkyl, $C_2$ to $C_{10}$ alkenyl, $C_2$ to $C_{10}$ alkynyl,--

In Claim 1, Column 31, at Line 25, please delete:
"COO-alkylm $NH_2$,"
And insert:
--COO-alkyl, $NH_2$,--

In Claim 1, Column 31, at Line 31, please delete:
"wherein one of X and Z is bonded at the 5'-position to the"
And insert:
--wherein one of X and Z is bonded at the 5'-position of the--

In Claim 28, Column 32, beginning at Line 42 and ending at Line 43, please delete:
"wherein R is a terminal alkyne."
And insert:
--wherein R comprises a terminal alkyne.--

Signed and Sealed this
Twelfth Day of November, 2019

Andrei Iancu
*Director of the United States Patent and Trademark Office*

In Claim 32, Column 33, beginning at Line 5 and ending at Line 23, please delete:
"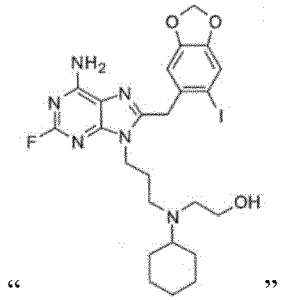"
And insert:
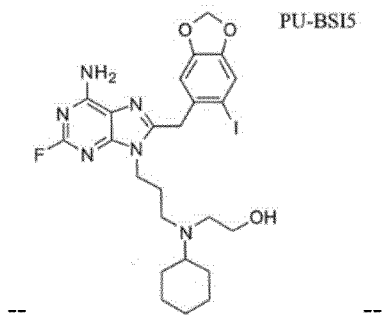
--  --
In Claim 46, Column 36, at Line 25, please delete:
"and/pr"
And insert:
--and/or--